United States Patent [19]

Flewelling et al.

[11] Patent Number: 5,231,591
[45] Date of Patent: * Jul. 27, 1993

[54] AGENT GAS ANALYZER AND METHOD OF USE

[75] Inventors: Ross F. Flewelling, Oakland; Eric T. Johansson, Dublin; Lucille A. Ferus, Oakland; John A. Culver, San Francisco; Keith H. Breton, San Ramon, all of Calif.

[73] Assignee: Nellcor Incorporated, Hayward, Calif.

[*] Notice: The portion of the term of this patent subsequent to Sep. 3, 2008 has been disclaimed.

[21] Appl. No.: 726,430

[22] Filed: Jul. 5, 1991

Related U.S. Application Data

[63] Continuation of Ser. No. 406,230, Sep. 11, 1989, Pat. No. 5,046,018.

[51] Int. Cl.⁵ .................... G01N 21/35; G06F 15/42
[52] U.S. Cl. .................... 364/497; 128/719; 364/413.03
[58] Field of Search .................... 364/413.02, 413.03, 364/496–499; 250/338, 339, 343, 344, 345; 356/51, 437; 128/719; 422/83

[56] References Cited

U.S. PATENT DOCUMENTS

| 3,877,812 | 4/1975 | Thompson | 250/339 |
| 3,968,367 | 7/1976 | Berg | 250/343 |
| 4,013,260 | 3/1977 | McClatchie et al. | 364/497 |
| 4,180,734 | 12/1979 | Gedeon | 128/719 |
| 4,229,968 | 10/1980 | Muldoon | 364/497 |
| 4,467,435 | 8/1984 | Warnke et al. | 364/497 |
| 4,578,762 | 3/1986 | Wong | 364/497 |
| 4,648,396 | 3/1987 | Raemer | 250/343 |
| 4,692,621 | 9/1987 | Passaro et al. | 250/343 |
| 4,817,013 | 3/1989 | Corenman et al. | 250/343 |
| 4,881,183 | 11/1989 | Groe | 364/497 |
| 4,907,166 | 3/1990 | Corenman et al. | 364/497 |
| 4,914,719 | 4/1990 | Conlon et al. | 250/343 |
| 4,914,720 | 4/1990 | Knodle et al. | 128/719 |
| 4,932,402 | 6/1990 | Snook et al. | 364/413.03 |
| 5,003,985 | 4/1991 | White et al. | 364/413.03 |
| 5,046,018 | 9/1991 | Flewelling et al. | 364/497 |

Primary Examiner—Kevin J. Teska
Attorney, Agent, or Firm—Townsend and Townsend Khourie and Crew

[57] ABSTRACT

An agent gas analyzer that will determine the types and measure simultaneously the concentrations of a plurality of agent gases in a respiratory gas stream of an anesthetized patient, with the analyzer self-determining the agent gas types and concentrations each time gas measurements are made.

21 Claims, 22 Drawing Sheets

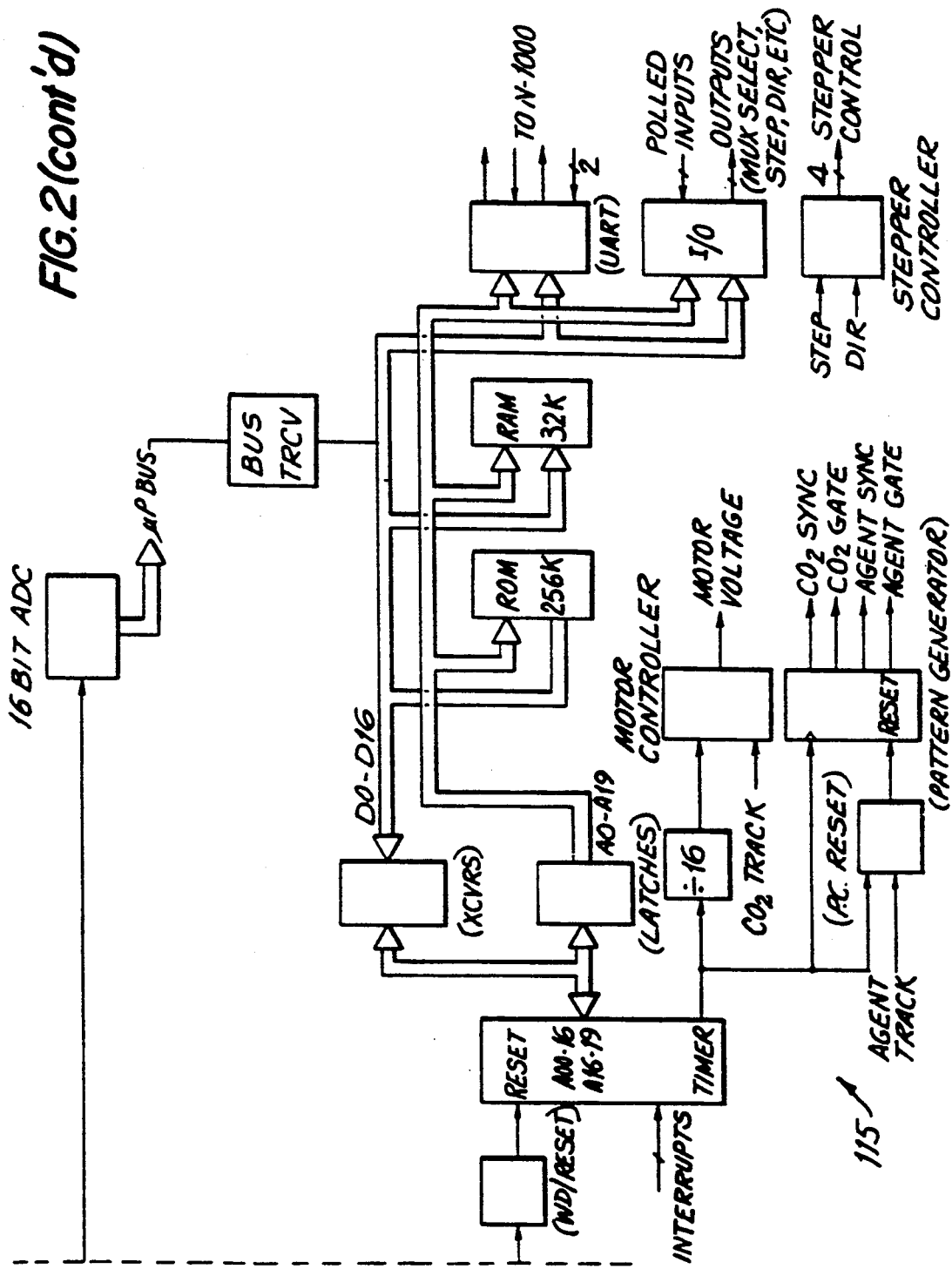

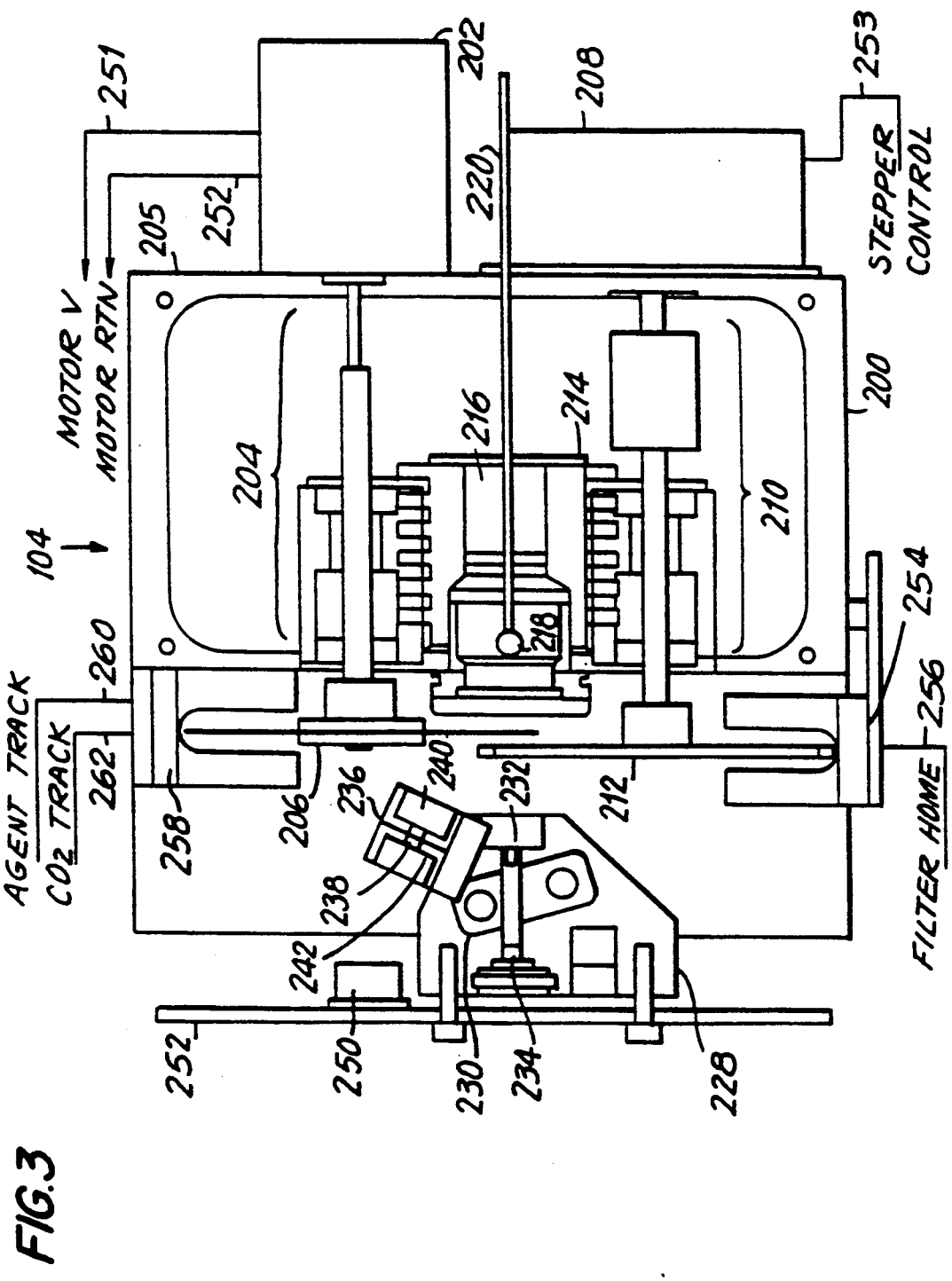

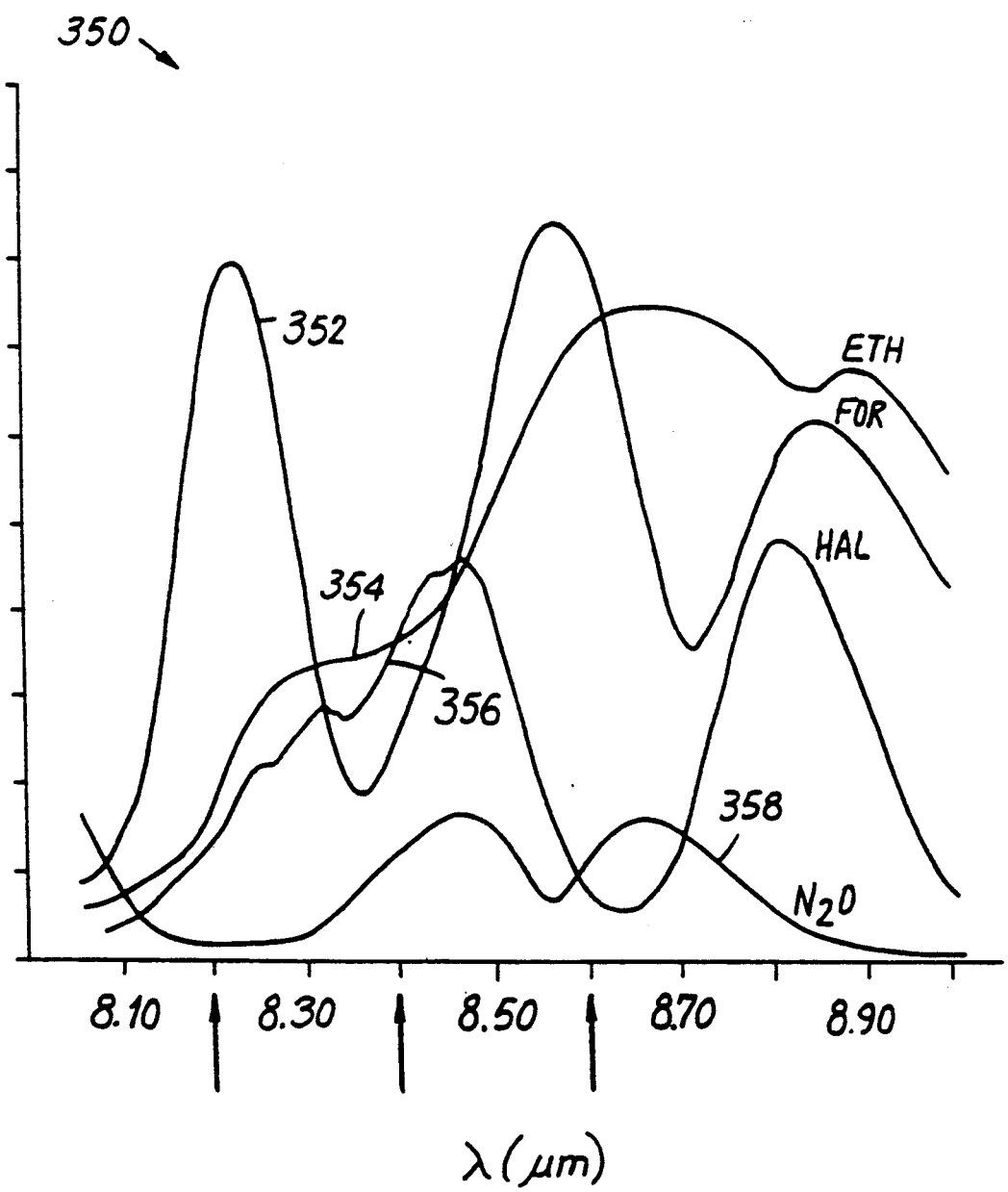

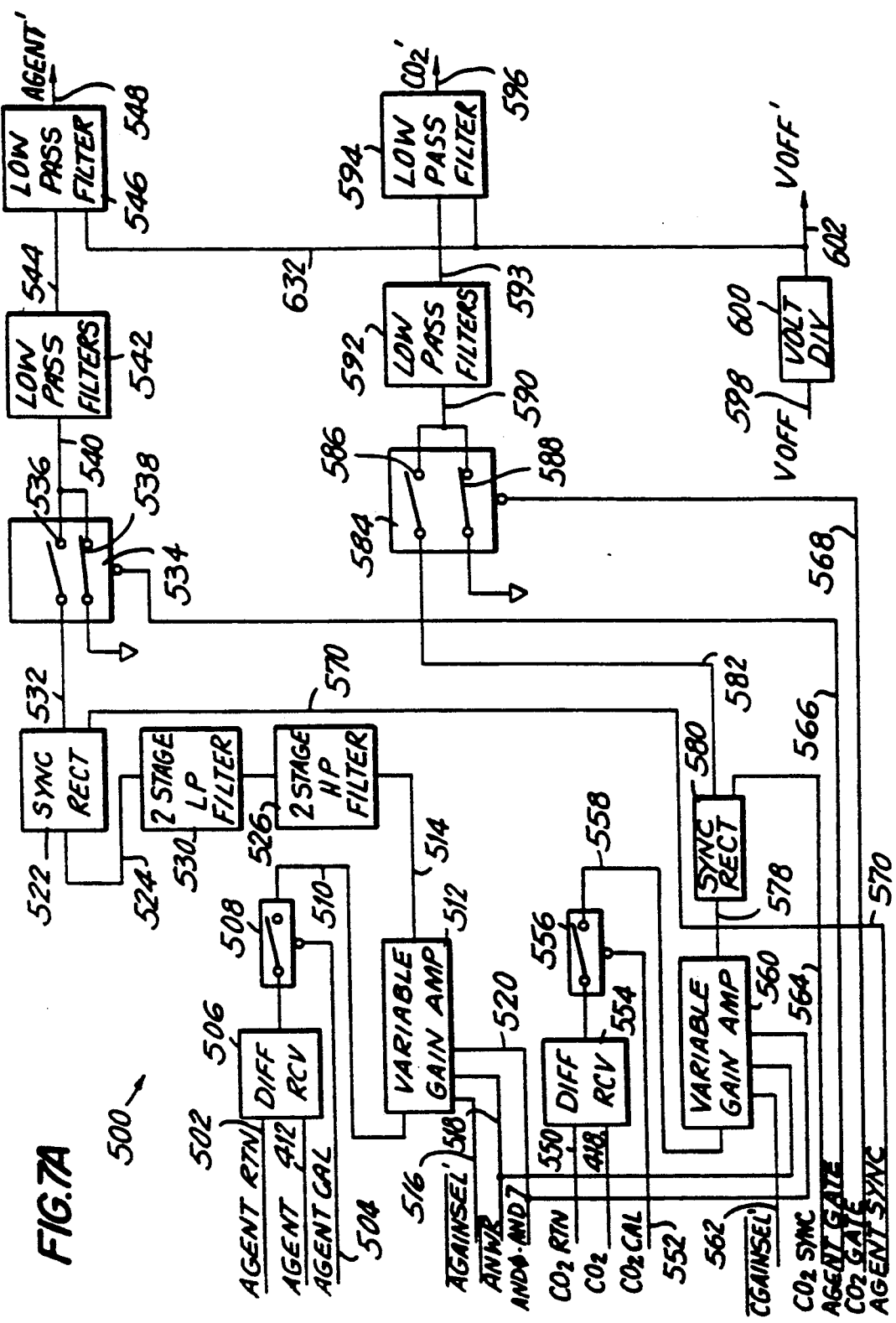

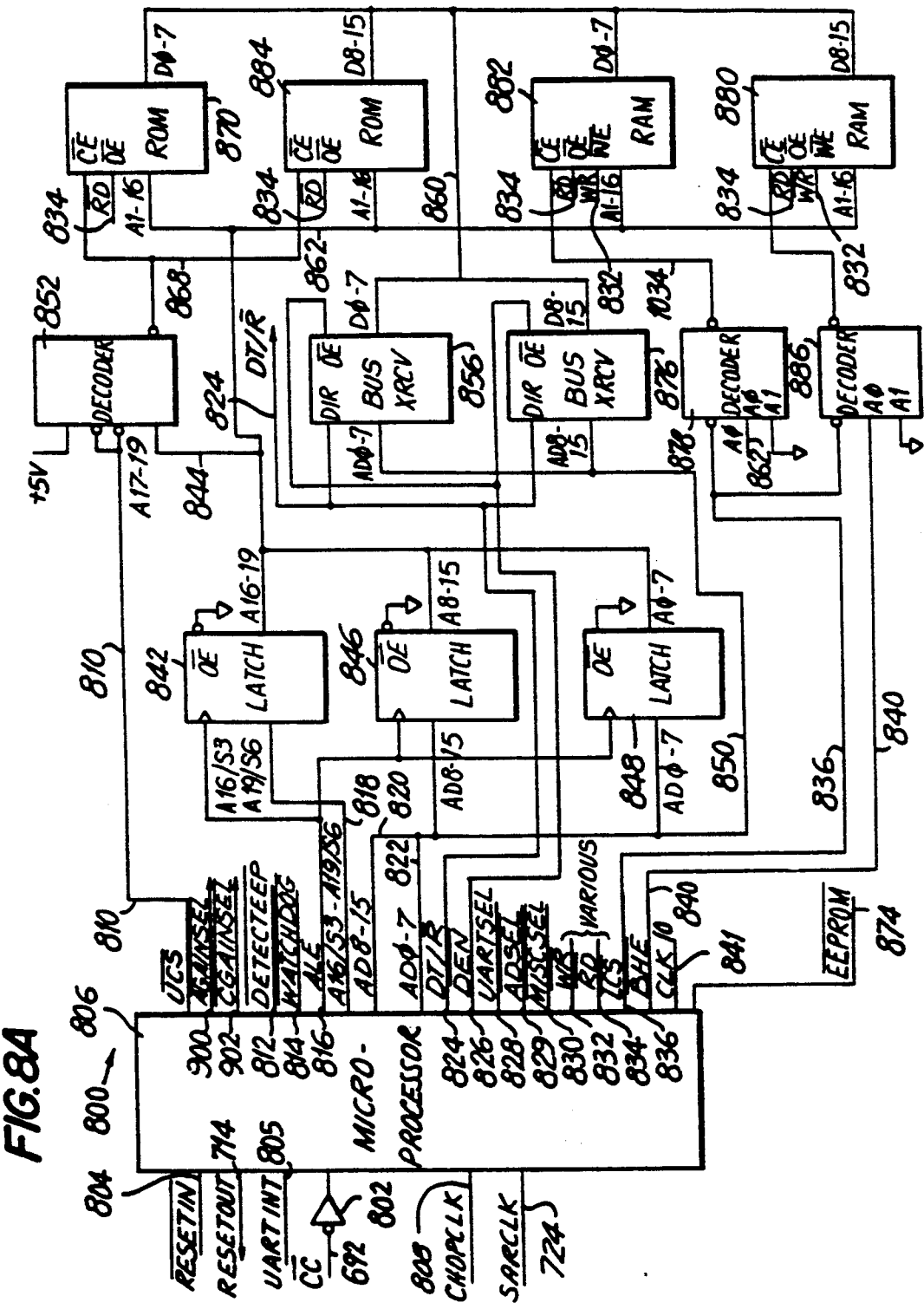

AGENT GAS ANALYZER AND METHOD OF USE

This is a continuation of application Ser. No. 07/406,230 filed Sep. 11, 1989 now U.S. Pat. No. 5,046,018.

FIELD OF THE INVENTION

The present invention relates to a class of instruments referred to as gas analyzers which are used for measuring the concentration or partial pressure of a gas in a gas stream. More specifically, the present invention relates to an infrared gas analyzer that simultaneously measures the concentrations of a plurality of anesthetic agent gases in the respiratory gas stream of an anesthetized patient.

BACKGROUND OF THE INVENTION

Patients that are anesthetized during surgery are usually intubated. It has been desirable to measure the respiratory gases of such patients to determine the constituents of the respiratory gas. Specifically, analysis of the inspired and expired respiratory gas provides information regarding the amount of carbon dioxide ($CO_2$), nitrous oxide ($N_2O$), and anesthetic agents the respiratory gas contains.

Anesthetic agents are present as a single agent gas or as a mixture of a number of agent gases during transition from one type of agent gas to another. Three of the most common anesthetic agent gases, other than nitrous oxide, are halothane, enflurane, and isoflurane. The agent gas that is administered to a patient must be carefully controlled by an anesthesiologist because of the great risk of supplying too much or too little. If too much is supplied the patient may die and if too little is supplied the patient may be subjected to needless pain.

In the past, the gas analyzers that were used to measure agent gases were the same devices that were used to measure end-tidal $CO_2$ and $N_2O$. These devices include mass spectrometers and non-dispersive infrared gas analyzers infrared gas analyzer").

Mass spectrometers that are used for such gas measurements are usually part of operating room suites in which one spectrometer is shared among many rooms. Though a mass spectrometer measures a multiplicity of gases, it has the disadvantages of cost, maintenance and calibration requirements, slow response time, and non-continuous measurement. Infrared gas analyzers, though having the ability to measure the concentrations of inspired and end-tidal $CO_2$ and $N_2O$, have not in the past simultaneously measured, or identified, multiple agent gases in real-time.

The present invention overcomes these and other problems of prior art devices that have been used to measure respiratory gases as will be shown in the remainder of the specification and in the attached drawings.

SUMMARY OF THE INVENTION

The present invention is an agent gas analyzer that simultaneously measures a plurality of agent gases in a patient's respiratory gas stream.

The agent analyzer of the present invention includes an agent optical bench, analog circuits, and processing circuits. The agent optical bench has a single infrared source for providing light to an agent optical path and a $CO_2$ optical path. The agent optical bench has a chopper wheel for interrupting the light at regular intervals. The chopped light is then passed to respective detectors of the agent optical path and the $CO_2$ optical path. The chopper wheel is driven by a D.C. motor.

A filter wheel driven by a stepper motor indexes four filters into the agent optical path. Three of the filters pass light in three discrete narrow bandwidths in which light will be absorbed, and the fourth filter is a reference filter that passes light at a frequency that will not be absorbed by the agent gases of interest.

The respiratory gas that is analyzed is provided from an off analyzer source. This external source inputs the respiratory gas stream to agent analyzer gas pathway which includes a $CO_2$ measuring section and an agent measuring section. The gas passes through the $CO_2$ section first then the agent section. After leaving the agent section, the respiratory gas is returned to the external apparatus.

The agent optical bench includes circuits that are on a detection PCB ("DPCB"). These circuits include detectors for generating analog signals related to the partial pressures of $CO_2$ and agent gas in the gas stream. The DPCB also has circuits for generating analog signals representative of the bench temperature, pressure in the gas pathway, and timing signals.

An electrically erasable read-only memory (EEPROM) on the DPCB stores characterization information for the specific agent optical bench, pressure offset, nitrous oxide, and span. The characterization information corrects the measurements for analyzer performance that deviates from ideal theoretical performance. The characterization information obviates the need for calibration of the agent analyzer. This data is supplied to the processing circuits along with the other measured data.

The analog circuits are electrically connected to the agent optical bench and the processing circuits. The analog circuits receive the output signals from the agent optical bench and, among other things, convert those signals from analog to digital signals.

The processing circuits include a microprocessor that performs the calculating functions according to a predetermined method. The outputs of the processing circuits are the concentrations of the agent gases corrected for the temperature of the optical bench, nitrous oxide, span, pressure offset, and characterization. These signals, along with the measured values of temperature, and pressure, are output to an external device for display, storage or analysis.

The agent gas analyzer of the present invention may be connected pneumatically and electrically to an infrared gas analyzer such as the one disclosed in co-pending U.S. patent application Ser. No. 101,931, filed Oct. 17, 1987, also assigned to the assignee of the present application. The gas pumping system and the display circuitry of such a gas analyzer may be used by the agent gas analyzer of the present invention. The pumping system is used for delivering both respiratory gas and zero calibration gas (scrubbed room air) to the agent gas pathway. The display circuitry and the display screen are used for displaying the concentrations of halothane, enflurane, and isoflurane and other agent gas information.

In operation, the agent analyzer will generate the concentrations of halothane, enflurane, and isoflurane using up to third order matrix analysis. In the preferred method of operation, the I/E (inspired/expired) mode, the analysis procedure changes depending on whether there is sufficient time during a respiratory period for one, two, or three of the measuring filters to be cycled through an agent gas optical path. If only one filter is to be cycled, the other two filter values needed to calculate the agent gas concentrations are determined by an interpolation method. If only two filters can be cycled, the remaining filter value is determined by an interpolation method. When all three filters are cycled in a single measuring period, the full analysis can be performed with the measured values without the need for interpolation of one or more of the filter values.

An object of the present invention is to provide an agent gas analyzer for measuring simultaneously a plurality of agent gases in a respiratory gas stream.

Another object of the present invention is to provide an agent gas analyzer which has different methods of determining the concentrations of a plurality of agent gases in a respiratory gas stream depending on the number of filters that are cycled through an agent gas optical path during a particular gas measurement period.

A further object of the present invention is to provide an agent gas analyzer which uses up to third order matrix analysis in determining the concentrations of a plurality of agent gases in a respiratory gas stream.

A still further object of the present invention is to provide an agent gas analyzer that determines the concentrations of a plurality of agent gases in a respiratory gas stream separately for inspired and expired phases of a patient's breath.

These and other objects of the present invention will be described more fully in the remainder of the specification and will be disclosed in the attached drawings.

BRIEF DESCRIPTION OF THE DRAWINGS

FIG. 3 is a detailed top perspective view of the agent gas optical bench of the present invention.

FIG. 5B is representative graph of the absorption spectra for the halothane, enflurane, and isoflurane.

FIGS. 7A and 7B are schematic drawings of the analog circuits of the agent gas analyzer of the present invention.

FIGS. 8A, 8B, and 8C are schematic drawings showing the processing circuits of the agent gas analyzer of the present invention.

DETAILED DESCRIPTION OF THE DRAWINGS

The present invention is an agent gas analyzer that will determine the type and measure simultaneously the concentrations of a plurality of agent gases in the respiratory gas stream of an anesthetized patient. The analyzer self-determines the type and concentrations for the plurality of agent gases each time agent gas measurements are made.

Figure 1:
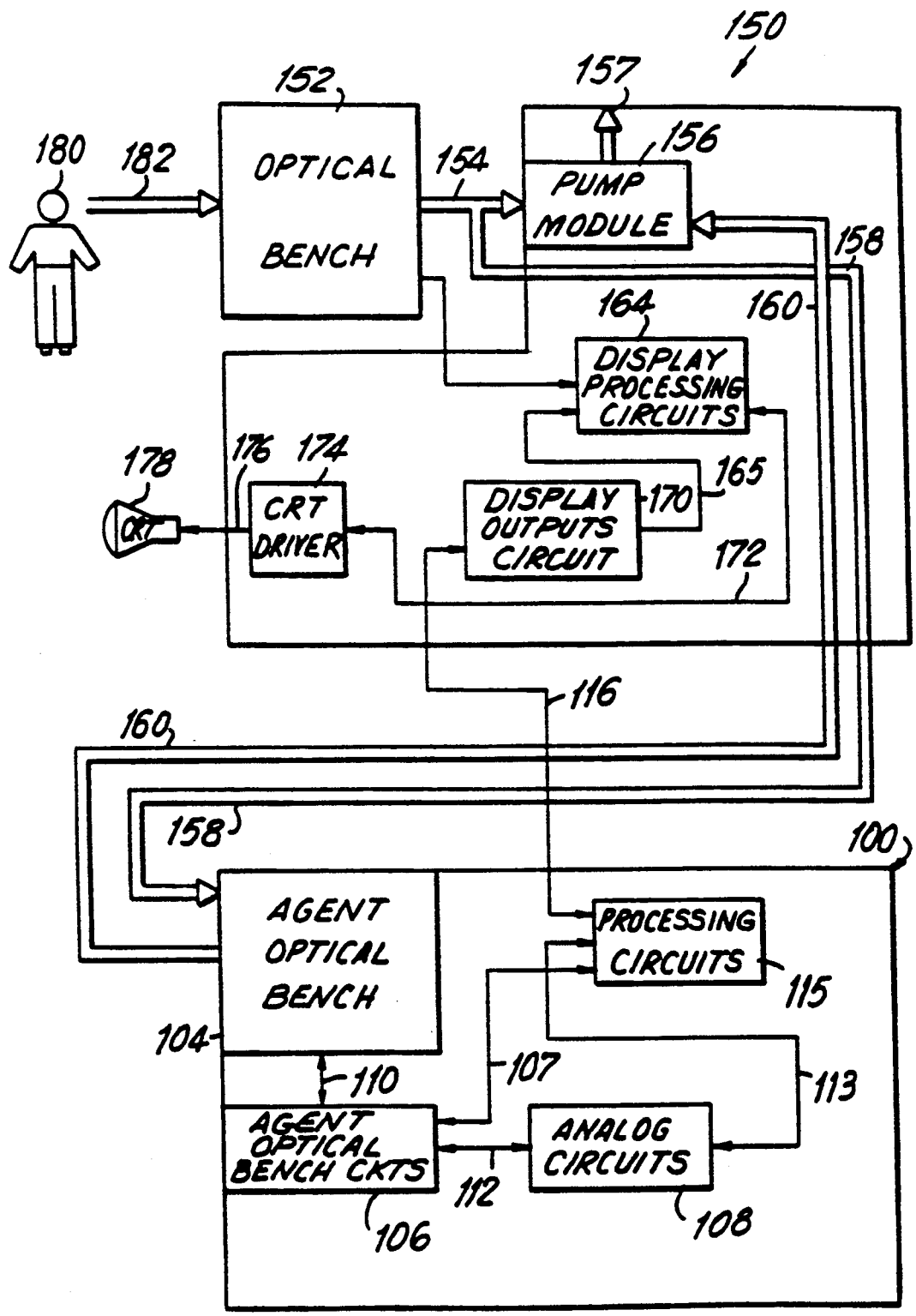
FIG. 1 is a block diagram of the agent gas analyzer of the present invention connected pneumatically and electrically to an infrared gas analyzer.

FIG. 1 shows agent gas analyzer 100 of the present invention connected to infrared gas analyzer 150. Agent gas analyzer 100 uses pump module 156 of analyzer 150 for delivering the respiratory gas stream of patient 180 or scrubbed room air for zero calibration gas readings to the agent gas pathway. Analyzer 100 also uses the display circuitry of analyzer 150 for processing the agent gas signals for display on CRT 178 of infrared gas analyzer 150. An infrared gas analyzer that is capable of being connected to agent gas analyzer 100 is the gas analyzer disclosed in co-pending application Ser. No. 101,931, filed Oct. 17, 1987 assigned to the assignee of the present invention. It is to be understood that the agent gas analyzer of the present invention may be electrically and pneumatically connected to other infrared gas analyzers as long as such infrared gas analyzer can deliver the respiratory gas and scrubbed room air to the agent gas pathway and process the agent signals generated by the agent gas analyzer for display of the agent gas concentrations.

Again referring to FIG. 1, anesthetized patient 180 has a respiratory gas drawn off by pump module 156. When the agent gas analyzer is not connected, the gas stream passes through sample tube 182, the gas pathway (not shown) of optical bench 152, and gas line 154 en route to pump module 156. The gas stream is then sent to a scavenging system via outlet gas line 157. When the agent gas analyzer is connected, the gas stream in gas line 154 will connect directly to line 158 to deliver the gas stream to agent gas analyzer 100. As the gas passes through the agent optical bench, $CO_2$ and agent gas measurements are made along with pressure and temperature measurements. The measured values are used in calculating the concentrations for the agent gases in the gas stream. After the gas stream passes through the agent gas pathway, it is sent to pump module 156 via gas line 160 for removal to the scavenging system.

When it is desired to make the zero calibration gas reading at the optical bench, a valve in optical bench 152 is closed and one is opened to draw scrubbed room air into line 154 and then line 158. This air is pumped through the agent gas pathway in the same manner as the respiratory gas stream.

Agent optical bench circuits 106 are electrically connected to agent optical bench 104 by line 110. The agent optical bench circuits process the agent gas signal, $CO_2$ gas signal, pressure signal, temperature signal, agent gas timing signal, $CO_2$ gas timing signal, and filter home signal for output to analog circuits 108 and processing circuits 115 of the agent gas analyzer.

The signals representative of the measured values for the agent gas, $CO_2$ gas, pressure, and temperature are input to analog circuits 108 via line 112. The agent timing, $CO_2$ timing, and filter home signals are input to processing circuits 115 on line 107. The analog circuits process the signals input thereto and in doing so convert them to digital signals. The processing circuits process signals output from the agent optical bench circuits to generate signals for demodulating the agent and $CO_2$ signals.

The digital signals input to processing circuits 115 on line 113 are processed to provide output signals on line 116 to the analyzer 150 that include the data necessary for display of the concentrations of the three agent gases, and alarm and information messages on the CRT 178.

Communications between display processing circuits 16 of analyzer 150 and processing circuits 115 of agent gas analyzer 100 are through display output circuits 170 and direct agent gas analysis on a non-conflict basis with the respiratory gas analysis being conducted by analyzer 150. Display processing circuits 164 of analyzer 150 generate output signals on line 172 representative of the agent gas concentrations for controlling the generation of control voltages in CRT driver 174. The control voltages output from CRT driver 174 on line 176 will cause display of at least the concentrations of the three agent gases on CRT 178.

Figure 2:
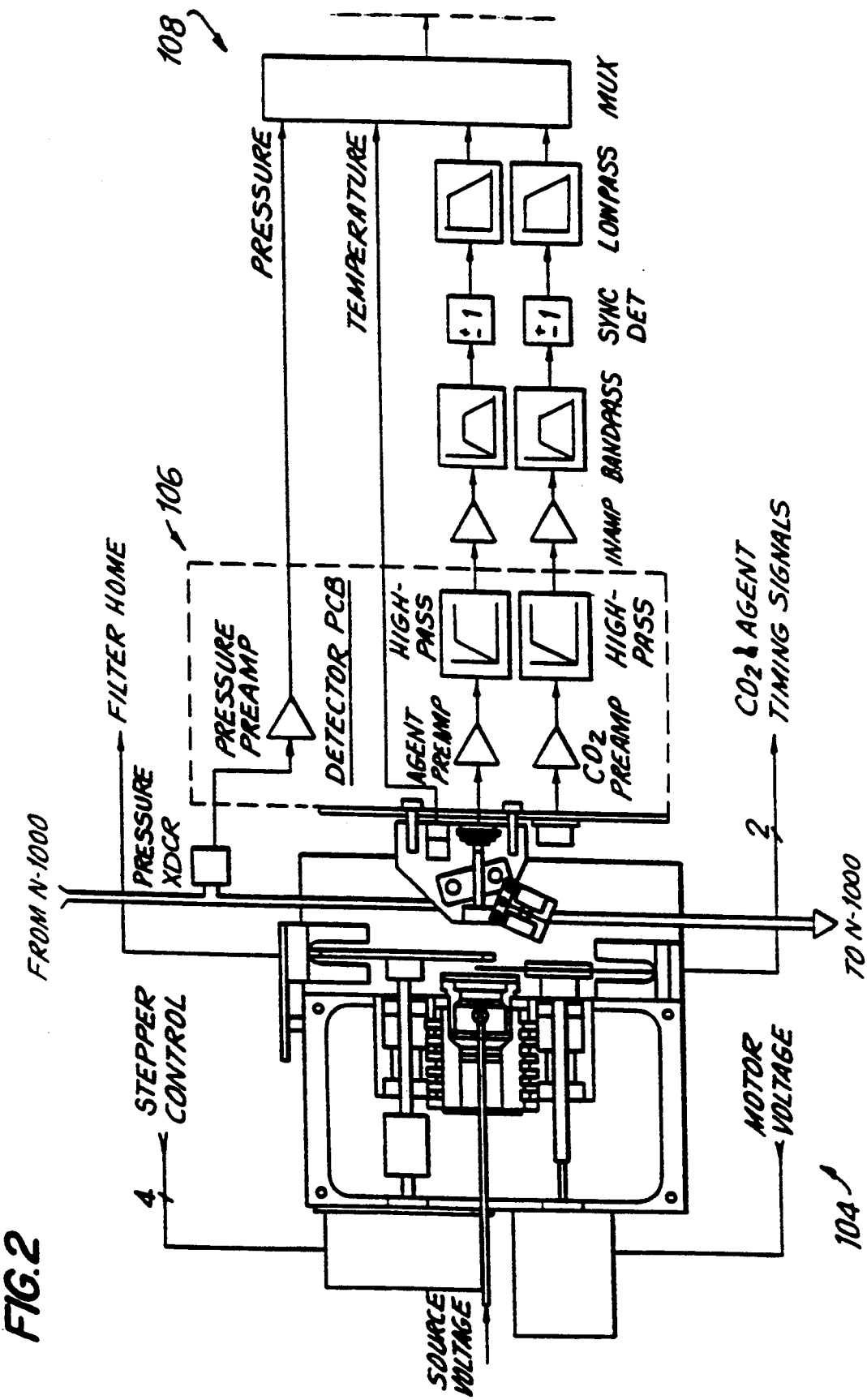
FIG. 2 is a diagram of the agent gas analyzer of the present invention with the agent gas optical bench shown in a cutaway top perspective view and the circuitry of the agent gas analyzer shown in block form.

FIG. 2 is a diagram of agent gas analyzer 100 with agent gas optical bench 104, agent optical bench circuits 106, analog circuits 108, and processing circuits 115 indicated. Each of these now will be described in detail.

Agent Optical Bench

Agent optical bench 104 will be described referring to FIGS. 3, 4, 5A, and 5B.

FIG. 3 is a perspective top cutaway view of agent optical bench 104. The bench has housing 200 with chopper wheel motor 202 and stepper motor 208 mounted in the rear sidewall. Coupling assembly 204 connects chopper motor 202 to chopper wheel 206. The chopper motor will rotate the chopper wheel at a rate determined by the MOTOR V signal on line 251 and the MOTOR RTN signal on line 252.

Coupling assembly 210 connects stepper motor 208 to filter wheel 212. The stepper motor is energized to step in a desired direction to place a particular filter in the agent gas optical path according to STEPPER CONTROL signals on line 253. This is representative of four power lines.

The chopper motor is a model 2022.814-12.562-000 commercially available from Maxon Motors, Burlingame, Calif. and the stepper motor is model 82-910 commercially available from Crouzet Controls, Inc., Schaumburg, Ill.

Heat sink 214 is disposed in the housing between coupling assemblies 204 and 210. Disposed in the opening of the heat sink that extends along the longitudinal centerline of the heat sink is infrared light source 216. The light source is powered via line 220. The light source provides infrared light through openings in the forward sidewall. The infrared light illuminates both the $CO_2$ and agent optical paths. The light source is preferably an infrared coilform light source that is commercially available from Buck Scientific, Inc., East Norwalk, Conn, under model number PE-12CIWL.

A fan may be disposed in a wall of the housing for cooling the inside of the housing. The fan is used for active temperature control. It is energized under software control to maintain the temperature within a predetermined range. In connection with the fan, a screen may be disposed on the opposite sidewall of the housing to further promote temperature control.

Agent flow block 228 contains agent section 230 of the agent gas pathway. Window 232 is disposed across a first end of the section. Detector 234 is disposed across the second end of the section. Agent section 230 has a gas inlet at a first end and a gas outlet at an opposite second end. The detector is mounted on the DPCB 252. Detector 234 is preferably a pyroelectric detector that is commercially available from Hiemann, GmbH, Wiesbaden, Germany under model number LHI807.

$CO_2$ flow block 236 contains $CO_2$ section 238 of the agent gas pathway. Window 240 is disposed across a first end of the section. $CO_2$ filter 242 is disposed at the second end of the section. $CO_2$ detector 250, which is mounted on DPCB 252, is in the $CO_2$ optical path. Detector 250 is preferably a lead selenide detector that is commercially available from New England Photoconductor, Norton, Mass. under model number FM-3.

In order to prevent background light from entering the $CO_2$ optical path, it may have a shield associated with the optics.

Preferably, gas line 158 from the pump module 156 connects to the inlet of the agent gas pathway. The agent gas pathway comprises the $CO_2$ section in the $CO_2$ flow block, the agent section in the agent flow block, and a jumper (not shown) that connects the outlet of the $CO_2$ section to the inlet of the agent section. The outlet of the agent section connects to return gas line 160 to the pump module. A pressure sensor is disposed across the gas pathway in the agent flow block for making pressure measurements of the agent gas pathway.

Light emitting diode (LED)/photodetector mount 254 has LED 402 (FIG. 6) and photodetector 404 (FIG. 6) mounted on opposing legs so that the filter wheel 212 may rotate between them. Single hole 318 (FIG. 5A) in filter wheel 212 is aligned with the optical path between the LED and photodetector. When the filter wheel is stepped so that the home or reference filter is in the agent optical path, hole 318 is in the optical path between the LED and photodetector. When this happens, the FILTER HOME signal on line 256 is asserted. This signal is supplied to processing circuits 115.

LED/photodetector mount 258 has LEDs 420 and 426 (FIG. 6) mounted in one leg and photodetectors 422 and 428 (FIG. 6) mounted in the opposite leg. Chopper wheel 206 rotates between the legs. LED 420 and photodetector 422 are aligned with $CO_2$ openings 304 (FIG. 4), and LED 426 and photodetector 428 are aligned with agent openings 300 (FIG. 4), in the chopper wheel. When one of the $CO_2$ openings is in the optical path between LED 420 and photodetector 422, the $CO_2$ TRACK signal on line 262 goes to a lower voltage. Similarly, when one of the agent openings is in the optical path between LED 426 and photodetector 428, the AGENT TRACK signal on line 260 goes to a lower voltage. These timing signals are input to two processing circuits for generating signals used for demodulating the detected $CO_2$ and agent gas signals, and signals for control of the chopper wheel.

Figure 4:
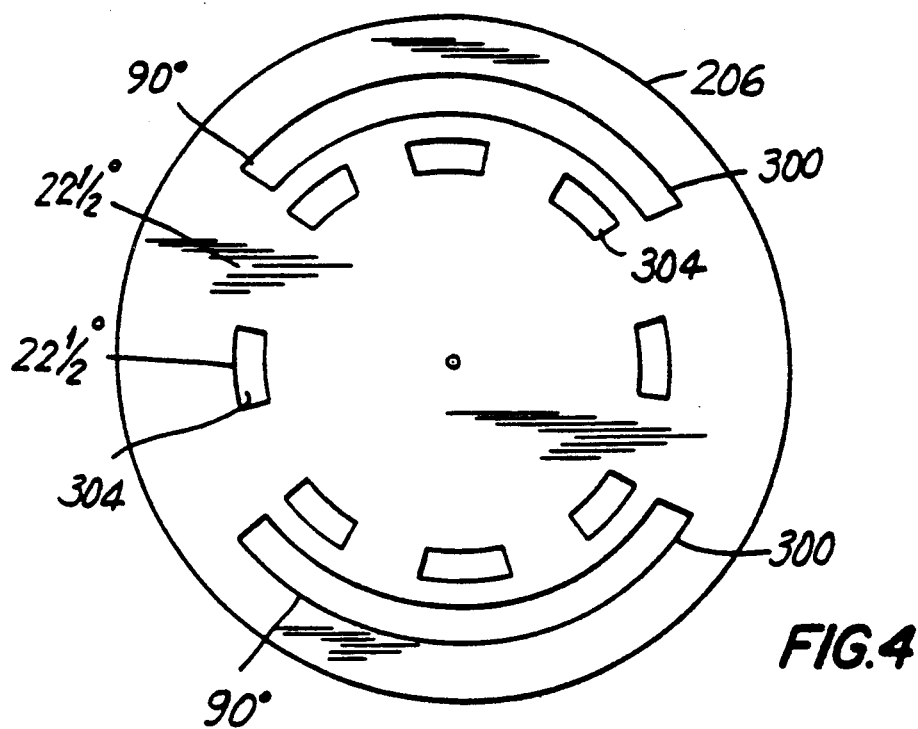
FIG. 4 is an end view of the chopper wheel of the optical bench of the agent gas analyzer of the present invention.

Referring to FIG. 4, chopper wheel 206 is shown. The chopper wheel has two groups of openings: agent openings 300 and $CO_2$ openings 304. Moving from the circumference toward the center of the chopper wheel, the first chopping means are agent openings 300. There are two agent openings. They are disposed opposite each other on the chopper wheel. Each opening subtends 90° and there are 90° between them.

The next chopping means toward the center of the chopping wheel are $CO_2$ openings 304. There are eight $CO_2$ openings. These openings are disposed equidistantly on the chopper wheel. Each $CO_2$ opening subtends $22\frac{1}{2}°$ and there are $22\frac{1}{2}°$ between adjacent openings.

Chopper motor 202 preferably rotates the chopper wheel at 20 revolutions per second. As such, the AGENT TRACK signal on line 260 preferably is a 40

Hz square wave signal and the $CO_2$ TRACK signal on line 262 is a 160 Hz square wave signal.

Figure 5A:
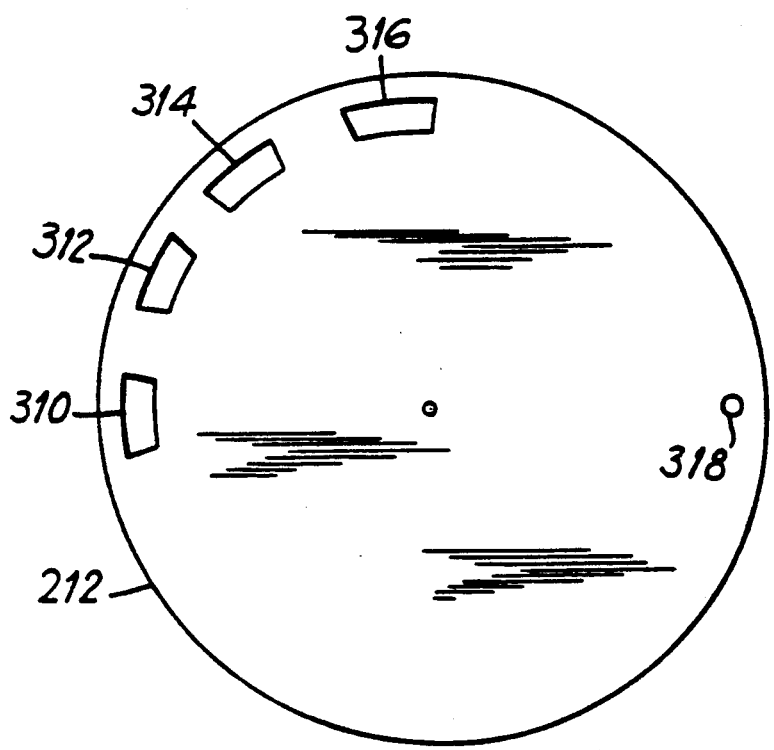
FIG. 5A is an end view of the filter wheel of the optical bench of the agent gas analyzer of the present invention.

Referring to FIG. 5A, filter wheel 212 is shown. The filter wheel has four filters disposed in it. Filter 310 is the reference filter, and filters 312, 314, and 316 are the three for passing light at three narrow bandwidths at which the agent gases of interest have predetermined absorptions. The filters are disposed in the agent gas optical path in accordance with a predetermined sequence as will be described subsequently.

It is to be understood that more or less than three filters may be used. The number of filters that are disposed in the filter wheel is determined by the number of agent gases whose concentration is desired to be determined. It is also to be understood that it is within the scope of the invention that other methods may be used to index the filters in the agent optical path, such as a linear method.

The filter wheel has hole 318 disposed in it. This hole is 180° from the home or reference filter. When the reference filter is in the agent optical path, hole 318 is in the optical path between LED 402 and photodetector 404. When this happens, the photodetector provides an output signal. The change in the signal output from the photodetector is a check to the microprocessor to confirm that the reference filter is in the agent gas optical path.

FIG. 5B is a graph of the absorption characteristics for halothane at 356, enflurane at 354, isoflurane at 352, and nitrous oxide at 358. Indicated along the abscissa are representative center frequencies for the three measuring filters. The wavelengths are selected at positions where at least one of the gases of interest has an absorption significantly different from the others. As stated, the reference filter is at a wavelength that the gases of interest will not be absorbed. As would be known by a person skilled in the art, the actual absorption would be corrected for the amount of nitrous oxide at the selected wavelengths.

Agent Optical Bench Circuits

Agent optical bench circuits 106 will be described referring to FIG. 6. The agent optical bench circuits comprise the circuitry that is mounted on the DPCB 252 (FIGS. 2 and 3), LED 402 and photodetector 404 in LED/photodetector mount 254, and LEDs 420 and 426 and photodetectors 422 and 428 in LED/photodetector mount 258. The analog signals output from the agent optical bench circuits are timing signals, detected gas signals, checking signals, and signals used for correcting the detected gas signals as will be described.

Figure 6:
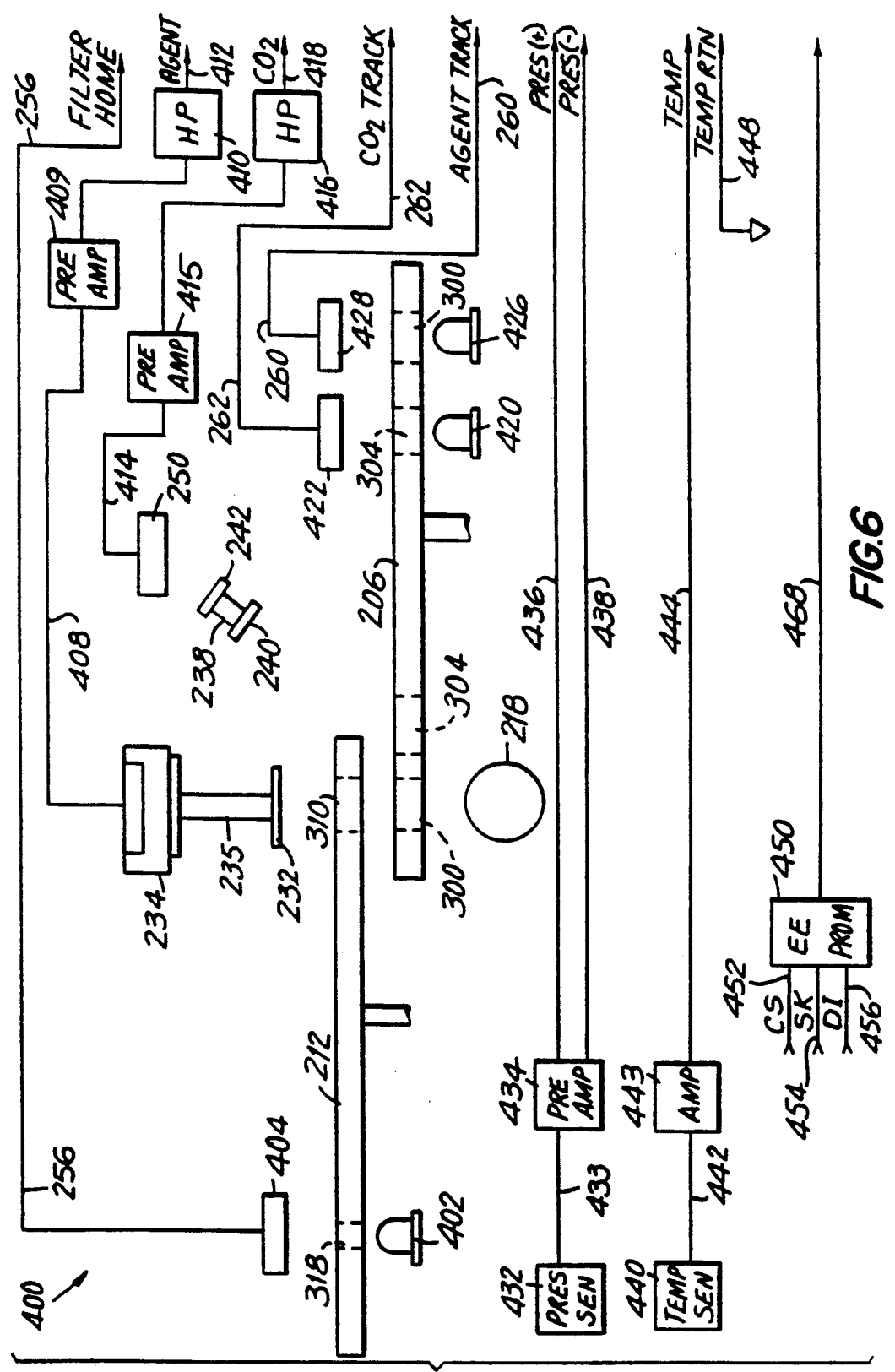
FIG. 6 is a schematic drawing of the agent optical bench circuits of the agent gas analyzer of the present invention.

The agent optical bench circuits are generally shown at 400 in FIG. 6. When filter wheel 212 has reference filter 310 in the agent gas optical path, hole 318 is in the optical path between LED 402 and photodetector 404. As such, light from LED 402 will issue on photodetector 404 causing it to provide a logic low output. The output is the FILTER HOME signal on line 256. The logic low for the FILTER HOME signal on line 256 is a check signal for the microprocessor of processing circuits 115 that in fact reference filter 310 is in the agent gas optical path as programmed.

The infrared light from the coilform 218 is directed along the agent and $CO_2$ gas optical paths. The light is chopped by the agent openings and the $CO_2$ openings in the chopper wheel. The chopped light in the agent optical path that issues on pyroelectric detector 234 causes a triangle wave output on line 408. The amplitude of the triangle wave will depend on the filter that is in the agent optical path as well as the amount of agent gas in the respiratory gas stream. The signal on line 408 is processed by preamplifier 409 and high pass filter 410. The output of high pass filter is a smooth triangle wave that is AGENT signal on line 412.

In a like fashion, the chopped light in the $CO_2$ optical path that issues on lead selenide detector 250 causes a square wave output on line 414. The amplitude of the square wave will depend on the absorption by the $CO_2$ gas in the $CO_2$ section of the gas pathway.

The signal on line 414 is input to preamplifier 415 and high pass filter 416. The output of the high pass filter is the smoothed square wave signal that is the $CO_2$ signal on line 418.

There are significant differences in the amplitude of the square wave signal output from the detector for the inspired and expired breath phases. Hence, the amplitude of the $CO_2$ signal may be used to indicate the parts of the AGENT signal on line 412 that are associated with the inspired and expired breath phases.

The light that issues on the photodetector 422 from LED 420 is chopped by $CO_2$ openings 304. The square wave output of photodetector 422 is the $CO_2$ TRACK signal on line 262 which is the $CO_2$ timing signal. The light that issues on the photodetector 428 from LED 426 is chopped by agent openings 300. The square wave output of photodetector 428 is the AGENT TRACK signal on line 260 which is the agent timing signal. The $CO_2$ TRACK is used for control of the chopper motor speed. The AGENT TRACK signal is used for generating the $CO_2$ GATE, $CO_2$ SYNC, AGENT GATE, and AGENT SYNC signal waveforms for demodulating the detected $CO_2$ and AGENT signals.

The pressure in the agent gas pathway is sensed by pressure sensor 432. The sensed signal is input to preamplifier 434 on line 433. The output of preamplifier 434 is the PRES(+) signal on line 436 and the PRES(−) signal on line 438.

Pressure sensor 432 is an absolute pressure measuring type pressure sensor. The pressure sensor is commercially available from IC Sensors, Inc., Sunnyvale, Calif.

The pressure is continuously monitored during system operation. Rapid pressure changes may indicate various problems in the agent optical bench. The pressure within the agent optical bench must be considered in calculating the agent gas concentrations.

The pressure sensor also measures barometric pressure when desired. This value is stored in memory for later use. The stored value for barometric pressure is updated at predetermined times.

The agent optical bench temperature is sensed by temperature sensor 440. The sensed temperature (in volts) on line 442 is input to amplifier 443. The output of amplifier 443 is the TEMP signal on line 444. Associated with the TEMP signal on line 444 is the TEMP RTN signal on line 448. This signal is tied to ground. Preferably, temperature sensor 440 is commercially available form Analog Devices, Norwood, Mass. under model number AD592CN.

EEPROM 450 stores coefficients relating to characterization of the agent optical bench. The characterization coefficients do not adjust or change the operation of any component of the optical bench or the apparatus as a whole. These coefficients correct the bench's measurements for system component deviation from ideal.

The inputs to EEPROM 450 are the DI data bus signal on line 456, the SK (serial data clock) signal on line 454, and the CS (chip select) signal on line 452. The CS and SK signals control the EEPROM's output. The DI signal is the data input to the EEPROM. These three signals are output from processing circuits 115. When properly instructed, the EEPROM outputs the characterization coefficients or other stored data on line 458 as the DO signal.

Analog Circuits

Analog circuits 108 will be described referring to FIGS. 7A and 7B. In the circuit in FIG. 7A, the AGENT signal on line 412 and the $CO_2$ signal on line 418 are similarly demodulated except that the AGENT signal undergoes more filtering than the $CO_2$ signal.

AGENT signal on line 412 is input to differential receiver 506. The second input to differential receiver is the AGENT RTN signal on line 502. The AGENT RTN signal is tied to ground. The output of differential receiver 506 is input to electronic switch 508. The control input to electronic switch 508 is the AGENT CAL signal on line 504. The AGENT CAL signal will have the proper logic state to open the switch when it is desired to determine the offset voltage of the agent gas channel, as will be described subsequently; otherwise the switch is closed.

The output of electronic switch 508 is input to variable gain amplifier 512.

The control inputs to variable gain amplifier 512 are the AGAINSEL' bar signal on line 516, the ANWR bar signal on line 518, and the parallel 8-bit data bus signal AND0-7 on line 520. AGAINSEL' bar signal is input to the CE bar input, the ANWR bar signal is input to the WR bar input, and the AND0-7 is input to the parallel 8-bit input of the amplifier. When the AND0-7 signals are written into the amplifier, it will have a gain from 0 to 12 based on their values. (The "bar" designation after a signal or input name indicates the inverted state of the signal or input without the bar designation, as is known by those skilled in the art.)

The output of variable gain amplifier 512 on line 514 is input to two stage high pass filters 526 and then to two stage low pass filters 530. This filtering will provide a clean sine wave AGENT signal. The output of the two stage low pass filters on line 524 is input to synchronous rectifier 522. Synchronous rectifier 522 demodulates the AGENT signal. The demodulating signal input to synchronous rectifier 522 is the AGENT SYNC signal on line 570. The AGENT SYNC signal has a +1 value during the agent gas period and a −1 value during the dark period. Accordingly, the dark period signal is inverted while the gas period signal values are not.

The demodulated AGENT signal output from synchronous rectifier 522 on line 532 is input to double switch 534. The switch elements double switch 534 are oppositely disposed. That is, switch element 536 is open and switch element 538 is closed. When the value of the control input to double switch 534 changes, the switch elements will be change their respective open or closed positions.

The control input to double switch 534 is the AGENT GATE signal on line 566. The AGENT GATE signal controls the disposition of switch element 536 and 538 according to its predetermined waveform. The output of the switch is the gated AGENT signal on line 540.

The signal output from double switch 534 is input to low pass filters 542. The signal output from the low pass filters on line 544 is input to low pass filter 546. The second input to low pass filter 546 is the $V_{OFF}'$ signal on line 602. $V_{OFF}'$ signal is input to low pass filter 546 to insure that its output is never less than zero.

The $V_{OFF}'$ signal on line 602 is the $V_{OFF}$ signal on line 598 divided down by voltage divider 600 to 120 mV.

After gating, the AGENT signal has a rectified sinusoidal waveform with an amplitude determined by the filter that was in the agent optical path. After filtering, the waveform output for the agent gas on line 548 is a changing waveform corresponding to the detected value for agent gas.

The $CO_2$ signal on line 418 is input to differential receiver 554. The second input to differential receiver 554 is the $CO_2$ RTN signal on line 550. The $CO_2$ RTN signal is tied to ground. The output of differential receiver 554 is input to electronic switch 556. The control input to electronic switch 556 is the $CO_2$ CAL signal on line 552. The $CO_2$ CAL signal will have the proper logic state to open the switch when it is desired to determine the offset voltage, as will be described subsequently. Otherwise, the switch is closed.

The output of electronic switch 556 on line 558 is input to variable gain amplifier 560. The control inputs to variable gain amplifier 560 are the CGAINSEL' bar signal on line 562, the ANWR bar signal on line 518, and the parallel 8-bit data bus signals AND0-7 on line 520. The CGAINSEL' bar signal is input to the CE bar unit, the ANWR bar signal is input to the WR bar input, and the AND0-7 is input to the parallel 8-bit input of the amplifier. When the AND0-7 signals are written into the amplifier, it will have a gain from 0 to 32 based on these values.

The output of variable gain amplifier 560 is input to synchronous rectifier 580. Synchronous rectifier 580 demodulates the $CO_2$ signal. The demodulating signal input to synchronous rectifier 580 is the $CO_2$ SYNC signal on line 564. The $CO_2$ SYNC signal has a +1 value during the $CO_2$ gas period and a −1 value during the dark period. The dark period signal is inverted while $CO_2$ gas period signal values are not.

The demodulated $CO_2$ signal output from synchronous rectifier 580 on line 582 is input to double switch 584. As shown, switch element 586 is open and switch element 588 is closed. When the value input to the control input of double switch 584 changes, the switch pair will be change their respective open or closed positions.

The control input to double switch 582 is the $CO_2$ GATE signal on line 568. This signal controls the disposition of switch elements 586 and 588 according to its waveform.

The signal output from double switch 584 on line 590 is input to low pass filters 592. The signal output from these low pass filters on line 593 is input to low pass filter 594. The second input to low pass filter 594 is the $V_{OFF}'$ signal on line 602. The $V_{OFF}'$ signal is input to low pass filters 594 to insure that its output is never less than zero.

After gating, the $CO_2$ signal has a square waveform with an amplitude determined by the absorbed $CO_2$. After filtering, the waveform output for the $CO_2$ gas on line 596 is a changing waveform corresponding to the detected value for the $CO_2$ gas.

Figure 7B:
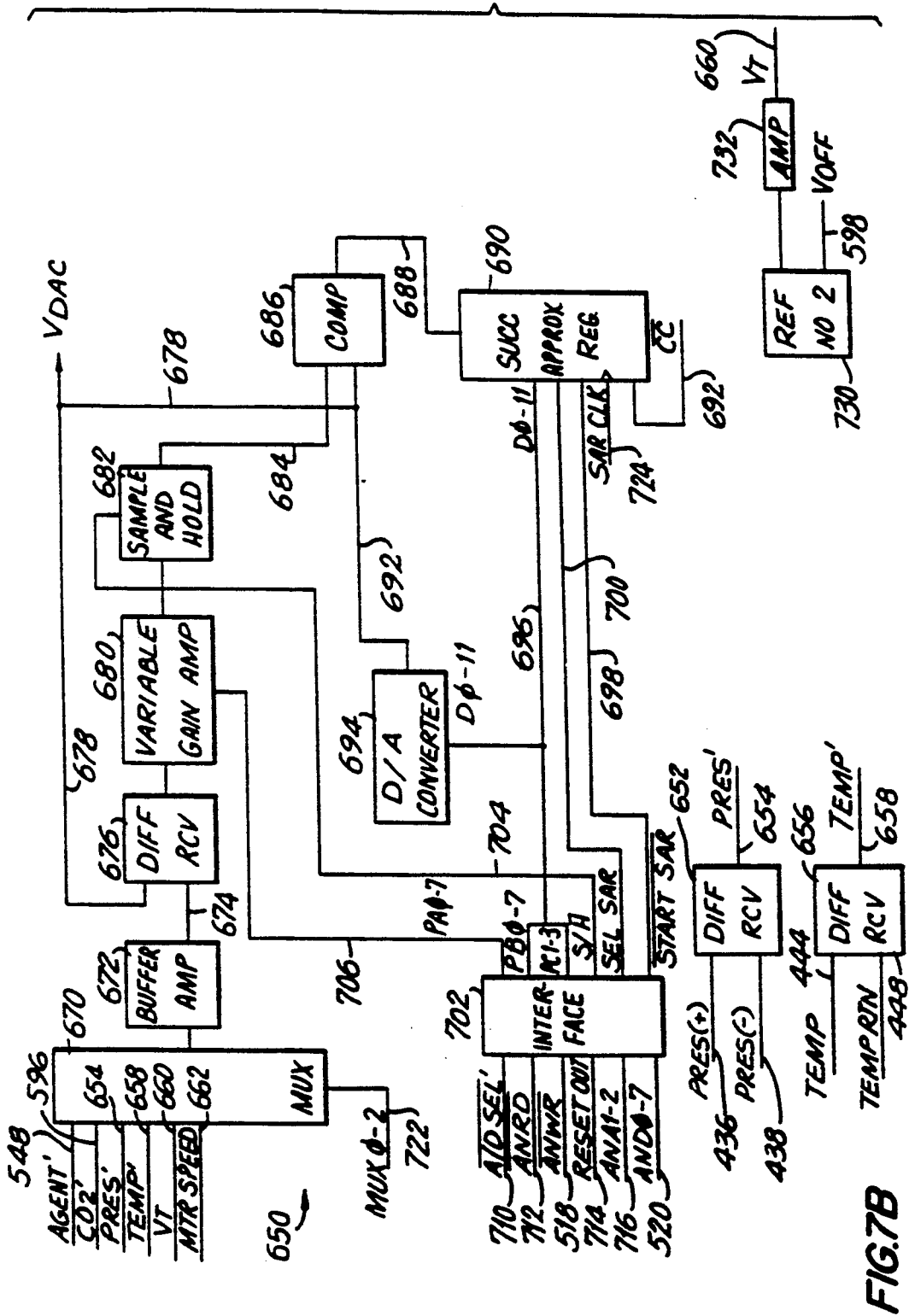

Referring to FIG. 7B, placement of the certain analog signals on to the analog circuits data bus will be described.

The inputs to multiplexer 670 are the AGENT' signal on line 548, the $CO_2'$ signal on line 596, the PRES' signal on line 654, the TEMP' signal on line 658, the $V_T$ signal on line 660, and the MTR SPEED signal on line 662. (Certain of these signals have been described while others have not; those that have not will be described.)

The PRES(+) signal on line 436 and the PRES(−) signal on line 438 are input to differential receiver 652. The output of differential receiver 652 on line 654 is the PRES' signal which is input to multiplexer 670.

The TEMP signal on line 444 and the TEMP RTN signal on line 448 are input to differential receiver 656. The output of the differential receiver is the TEMP' signal 658 which is also input to Multiplexer 670.

The temperature of the analog circuits is determined by REF-02, 730. The output of REF-02 is amplified by amplifier 732 and output therefrom as the $V_T$ signal on line 660. Also output from REF-02 is the $V_{OFF}$ signal on line 598. This signal is used for insuring that the outputs associated with the gated gas and reference signals are at least zero. REF-02 is commercially available from Precision Monolithics, Inc., Santa Clara, Calif.

The MTR SPEED signal on line 662 is the speed at which the chopper motor is turning the chopper wheel. The value is from processing circuits 115.

The parallel 3-bit signal MUXO-2 on line 722 from processing circuits 115 is input to the control inputs of multiplexer 670. Based on the logic states of these control signals, multiplexer 670 provides an output to buffer amplifier 672. The multiplexed analog signal includes the analog values for the detected partial pressures of the agent and $CO_2$ gases, the pressure in the gas pathway of the agent optical bench, temperature in agent optical bench, and the speed of the chopper motor.

The signals input to interface 702 are the ADSEL' bar signal on line 710, the ANRD bar signal on line 712, the ANWR bar signal on line 518, the RESETOUT signal on line 714, the parallel 2-bit address signal ANA1-2 on line 716, and the parallel 8-bit data bus signal AND0-7 on line 520. The outputs of interface 702 will be discussed subsequently in discussing the circuit.

The signal output from buffer amplifier 672 on line 674 is input to differential receiver 676. The second input to differential receiver 676 is the system offset signal VDAC on line 678 which is an output of digital to analog (D/A) converter 694. As used here the VDAC will identify the DC portion of the signal which should be removed to enhance the AC portion.

The channel offset signal for each of the two gas channels is generated by opening electronic switches 508 or 556 at an appropriate time (FIG. 7A). The voltage output by D/A converter 694 when these switches are open is that channel's voltage offset. The channel offset is subtracted from the measured values for agent and $CO_2$ gases.

The voltage difference output from differential receiver 676 is input to variable gain amplifier 680. The gain of the amplifier is controlled by the parallel 8-bit signal PA0-7 output from interface 702 on line 706. These signals are from data bus 520.

The output of variable gain amplifier 680 is input to sample and hold circuit 682. The sample and hold circuit control signal is the S/H (H bar) signal output from interface 702 on line 704. The control signal will cause the sample and hold amplifier to hold the output signal long enough for conversion of the current data in successive approximation register 690 and placement of that data on data bus 696.

The output of the sample and hold circuit is input to comparator 686. The second input to comparator 686 is the VDAC signal on line 678. The output of comparator 686 is input to successive approximation register 690. The START SAR bar signal on line 690 is input to successive approximation register 690 to start the analog to digital conversion process. The SELSAR signal on line 700 is input to the output enable input of successive approximation register 690. The logic value of this signal controls placement of the converted data on data bus 696.

Another output of successive approximation register 690 is the CC bar signal on line 692 which will be discussed in connection with FIG. 8A.

The SARCLK signal on line 724 is input to the clock input of the successive approximation register. The SARCLK signal determines the conversion time of the successive approximation register.

Processing Circuits

Figure 8B:
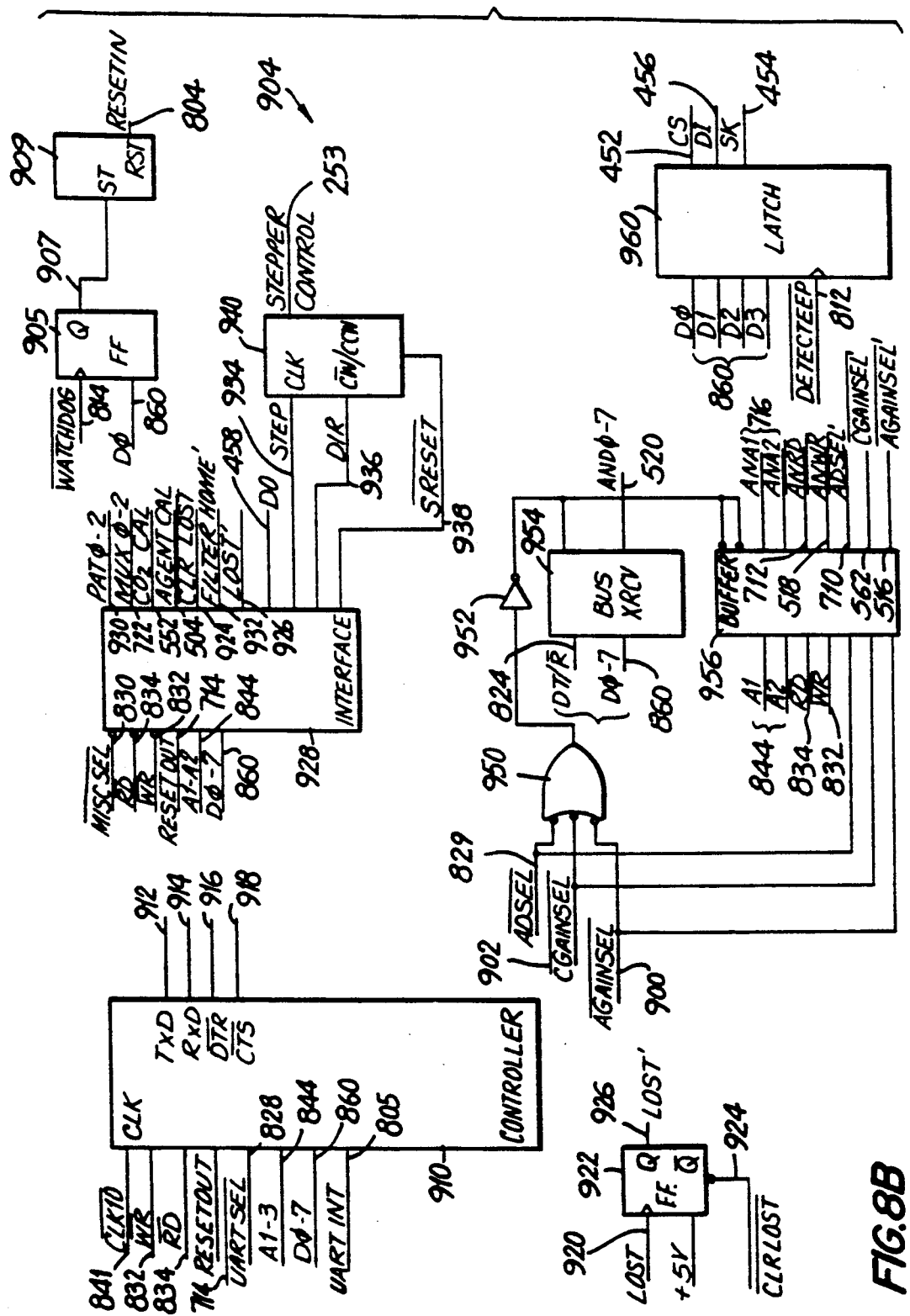
Figure 8C:
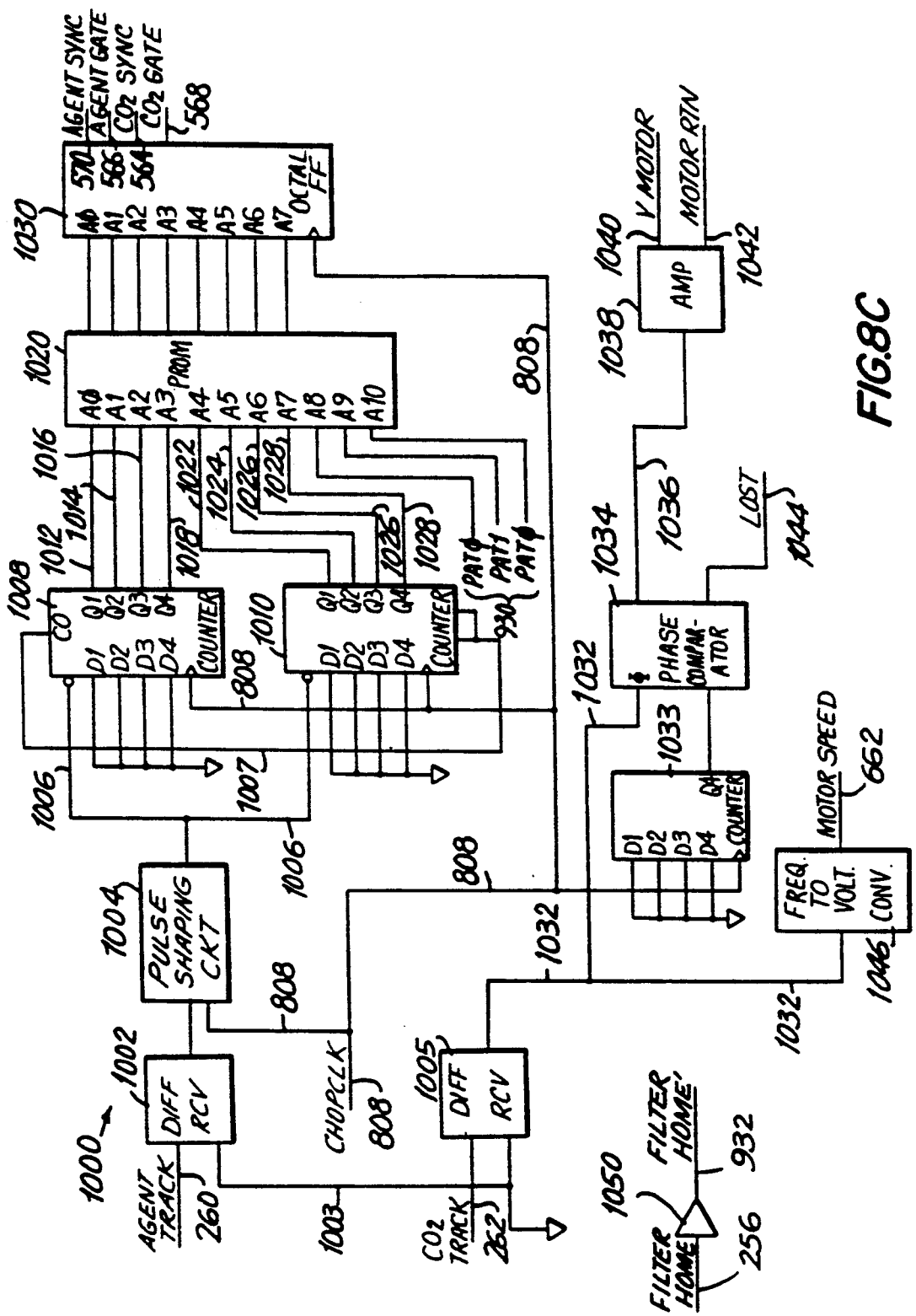

Referring to FIGS. 8A, 8B, and 8C, processing circuit 115 will be described.

Referring to FIG. 8A, one component of processing circuits 115 is microprocessor 806. Microprocessor 806 is a model 80186 CPU, commercially available from Intel Corp., Santa Clara, Calif. The microprocessor has a circuit associated with it that introduces a number of wait states when it communicates with controller 910. This circuit preferably is a PAL commercially available from Monolithic Memories, Santa Clara, Calif. under model number P16R6.

The signals input to microprocessor 806 are from other parts of the processing circuits shown in FIGS. 8B and 8C, and analog circuits 108. These are the RESETIN bar signal on line 804, the UART INT signal on line 805, and the CC bar signal on line 692.

The UART INT signal is an interrupt signal from controller 910 to indicate the transmission or receipt of data. The CC bar signal is an interrupt input from successive approximation register 690 to indicate completion of the conversion of an analog signal input, and that the converted signals are available on data bus 696. The RESETIN bar signal on line 804 is the signal that is generated by the watchdog circuit in FIG. 8B.

The output signals of microprocessor 806 are the UCS bar signal on line 810, the AGAINSEL bar signal on line 900, CGAINSEL bar signal on line 902, the DETECTEEP bar signal on line 812, the WATCHDOG bar signal on line 814, the ALE signal on line 816, the RESETOUT signal on line 714, the CHOPCLK signal on line 808, the SARCLK signal on line 724, the DT/R (R bar) signal on line 824, the DEN bar signal on line 826, the UART SEL signal on line 828, the ADSEL bar signal on line 829, the MISCSEL bar signal on line 830, the WR bar signal on line 832, the RD bar signal on line 834, the LCS bar signal on line 836, the BHE bar signal on line 840, and the CLK10 signal on line 841.

The UCS bar signal on line 810 enables decoder 852.

The AGAINSEL bar signal, the CGAINSEL bar signal, the ADSEL bar signal, the WR bar signal, the RD bar signal, and the address bus signals A1 and A2 are used for generating the AGAINSEL' bar signal on line 516, the CGAINSEL' bar signal on line 562, and the ADSEL' bar signal on line 710, the ANWR bar signal on line 518 and the ANRD bar signal on line 712 and the 2-bit analog address bus signals ANA1-2 for use by the analog circuits shown in FIGS. 7A and 7B.

The AGAINSEL' bar, CGAINSEL' bar, ADSEL' bar, and the MISCSEL bar signals are chip selection inputs for components of the analog circuits and processing circuits. The ANWR bar and ANRD bar signals act as conventional write and read signals.

The DETECTEEP bar signal on line 812 is the clock signal for the latch that contains the control signals for EEPROM 450. The WATCHDOG signal on line 814 is input to the clock input of flip flop 905 that is part of the circuit is used to generate the RESETIN bar signal for resetting the microprocessor.

The SARCLK signal on line 724 is input to the clock input to the successive approximation register. The CHOPCLK signal 808 is the reference clock signal for motor control. CLK10 on line 841 is input to a communications controller for generating its own internal clock.

The DT/R (R bar) signal controls the direction of data flow through bus transceivers 856, 876 and 954.

The DEN bar signal is the output enable signal for bus transceiver 856 and 876.

The LCS bar signal enables decoders 878 and 886.

The BHE bar signal is one of the control inputs to decoder 886.

The UART SEL signal is input to the chip select input of controller 910 of the processing circuits (FIG. 8B).

The ALE signal is for clocking address latches 842, 846, and 848.

The WR bar signal is the write timing signal indicating that the microprocessor is writing data into memory or into an input/output device.

The RD bar signal is a read timing signal indicating that the microprocessor is reading data.

Memory in FIG. 8A consists of two read only memories (ROMs) 875 and 884, and two random access memories (RAMs) 882 and 880. This memory is conventionally connected to address bus 844 and data bus 860.

FIG. 8A shows three address latches, 842, 846, 848. These latches are clocked by the ALE (address latch enable) signal input to their respective clock inputs. Hence, when the ALE signal has the proper logic state, the three latches are clocked simultaneously.

Latch 842 receives a parallel 4-bit input from address outputs A16/S3-A19/S6 on line 818. The clocking of latch 842 will place these values on address bus 844.

The parallel 8-bit information signal AD8-15, output from microprocessor 806 on line 820, is input to latch 846. The AD8-15 signal may contain either address or data information. When it is handling address information and those values are input to latch 846, when that latch is clocked, the latched address values are placed on address bus 844.

Similarly, the parallel 8-bit signal, AD0-7, output from microprocessor 860 on line 822, is input to latch 848. The AD0-7 signal may contain address or data information. When it contains address information and the values are input to latch 848, when that latch is clocked, the latched values are placed on address bus 844.

The AD0-15 signals also connect to data bus 860 via bus 850 and bus transceivers 856 and 876. Bus transceiver 856 controls transfers between the AD0-7 signals on bus 850 and the data bus. Bus transceiver 876 controls transfers between the AD8-15 signals on bus 850 and the data bus. Bus transceivers 856 and 876 are enabled by the DEN bar signal on line 826. The direction of the data transfer is controlled by the DT/R (R bar) signal on line 824.

Decoders 878 and 886 are used to enable RAMs 882 and 880, respectively. The LCS bar signal on line 836 enables both decoders. The first control signal input to decoder 878 is the A0 signal from the address bus. The second control input is tied to ground. These signals are decoded to provide an input to the chip enable input of RAM 882. Whether reading or writing is the proper action is determined by the logic states of the RD bar and WR bar signals input to RAM 882.

The first control signal input to decoder 886 is the BHE bar signal on line 840. The second control input is tied to ground. These signals are decoded to provide an input to the chip enable input of RAM 880. Similarly, whether reading or writing is accomplished depends on the logic states of the RD bar and WR bar signals input to RAM 880.

Third decoder 852 enables ROMs 870 and 884. The UCS bar signal output from microprocessor 806 on line 810 enables decoder 852. The control inputs to decoder 852 are the A17, A18 and A19 signals from address bus 844. When the control inputs are decoded, decoder 852 provides outputs to enable the ROMs. Whether an enabled ROM can be read depends on the logic state of the RD bar signal input to the OE bar input of each ROM.

FIG. 8B, includes circuits for that support microprocessors 806. Controller 910 provides output and input lines for communicating with all external devices, for example, a infrared gas analyzer. Specifically, through the controller, the microprocessor can send and receive data.

The CLK10 bar signal on line 841 is input to the clock input of controller 910.

The WR bar signal on line 832 and the RD bar signal on line 834 are input to controller 910. These signals control whether bus data is transmitted to, or received from, controller 910.

The RESETOUT signal on line 714 output from microprocessor 806 is input to controller 940.

The UART SEL bar signal on line 828 is input to controller 910 for chip selection and enabling reading from, or writing into, the controller.

The parallel 3-bit address bus signal, A1-3, from address bus 844 is input to controller 910. These are the address bus bits that control data flow. The parallel 8-bit data bus signal, D0-7, on line 860 also is input to controller 910. These are the data bus bits which are either read from or written onto.

The UART INT signal input from the controller on line 805 indicates to the microprocessor whether data has been transmitted or received.

The other signals that are output from, or input to, controller 910 are primarily associated with communicating with an external device. The signal on line 912 is the data that is transmitted, for example, from the agent gas analyzer to an infrared gas analyzer. The signal on line 914 is the data that is received by the agent gas analyzer. The signal on line 916 is output of the controller to indicate the agent gas analyzer that it is ready to receive data. The signal on line 918 is an input to the controller from an external device to indicate that it is clear to send data.

Flip flop 922 is for processing the LOST signal on line 920. The LOST signal will have a predetermined logic state when ever the speed of the chopper motor falls outside a predetermined window. The LOST signal is input to the clock input of flip flop 922. The "D" input of flip flop is connected to +5 v. On the positive going edge of the LOST signal the flip flop is clocked and the LOST' signal output for the "Q" output on line 926 will have a logic "1" value which will be placed on data bus 860 via interface 928. The flip flop may be cleared by the CLRLOST bar signal 924 once the chopper motor has again achieved the proper speed or at system shut down and restart.

Latch 960 is the latch for the control and data signals for EEPROM 456 of agent optical bench circuits 106. The signals input to the latch are the 4-bit data bus signal D0-3 on line 860 and the DETECTEEP bar signal on line 812. When the microprocessor desires certain information from the EEPROM, for example, for performing calculations, it will change the logic state the DETECTEEP bar signal on line 812. The changing of state will latch the new control and data signals. The outputs of the latch are the CS (chip select) control signal on line 452, the SK (serial data clock) control signal on line 454, and the data bus signal DI on line 456.

The watchdog circuit which comprises flip flop 905 and timer 909 is used to reset the microprocessor. At predetermined rate, microprocessor 806 changes the state of the WATCHDOG signal on line 814 the D0 signal of the data bus. This will continue to cause a changing waveform at the strobe input to the timer. If this changing waveform is not provided, the timer will time out causing the RESETIN bar signal output on line 804 to change state and reset the microprocessor. When this happens, it is an indication of a problem in the agent gas analyzer. The timer is commercially available from Dallas Semiconductor, Dallas, Tex. under Model Number DS1232.

Processing circuits 115 generate "select" signals, and the RD bar and WR bar signals for use by analog circuits 108. The processing circuits also provide the 2-bit address bus signal for use by the analog circuits.

The ADSEL bar signal on line 829, the CGAINSEL bar signal on line 902, and the AGAINSEL bar signal on line 900 are input to NAND gate 950 and to octal buffer 956. The other four inputs to octal buffer 956 are the A1 and A2 signals from address bus 844, the RD bar signal on line 834, and the WR bar signal on line 832.

The data bus signals D0-7 on line 860 are input to bus transceiver 954. The DT/R (R bar) signal on line 824 controls the direction of data flow through the transceiver. The output of NAND gate 950 is inverted by invertor 952 and input to the output enable inputs to bus transceiver 954 and octal buffer 956.

When at least one of the three "select" signals has the proper logic state, the bus transceiver and the octal buffer are output enabled; accordingly, data, control signals, and select signals are communicated between the analog circuits and processing circuits. On the analog circuits side, these signals are the AND0-7 data bus signal on line 520, the ANA1-2 address signal on line 716, the ANRD bar signal on line 712, the ANWR bar signal on line 518, the ADSEL' bar signal on line 710, the CGAINSEL' bar signal on line 562, and the AGAINSEL' bar signal on line 516.

Interface 928 communicates between microprocessor 806, and the analog circuits and other portions of the processing circuits. The inputs to interface 928 are the MISCSEL bar signal on line 830, the RD bar signal on the 834, the WR bar signal on line 832, the RESETOUT signal on line 714, the 2-bit address bus signal A1-2 on line 844, and the 8-bit data bus signal D0-7 on line 860. The MISCSEL bus signal is input to the chip select input of the interface. The RD bar signal and WR bar signal are input to the RD and WR inputs of the interface, respectively. The RESTOUT signal is input to the reset input, the A1-2 signal is input to the address bus inputs, and the D0-7 signal is input to the data bus inputs.

Other inputs to interface 928 are the FILTER HOME' signal on line 932, the LOST' signal on line 926, and the DO signal on the 458. The FILTER HOME' signal changes state when ever the reference filter is in the agent gas optical. The LOST' signal changes state when the chopper motor is not operating at the proper speed. The DO signal is the output signal for the EEPROM. All of these signals are provided to microprocessor so it can manage system operations and calculate agent gas concentrations.

The outputs of interface 928 are the 3-bit PAT0-2 signal on line 930, the 3-bit MUX0-2 signal on line 722, the $CO_2$ CAL signal on line 552, the AGENT CAL signal on line 504, the CLRLOST bar signal on line 924, the STEP signal on line 934, the DIR signal on line 936, and the SRESET bar signal on line 938.

The 3-bit PAT0-2 signal is input to PROM 1020 used in generating the gating and synchronization signals for demodulating the detected agent and $CO_2$ signals. The 3-bit MUX0-2 signal is the control signal for multiplexer 670. The $CO_2$ CAL and AGENT CAL signals are input to the electronic switch 556 and 508, respectively, for use in determining the offset voltages for the $CO_2$ and agent gas channels. The CLRLOST bar signal is used to reset flip flop 522 after the LOST' signal has changed state.

The STEP, DIR, and SRESET bar signals are for controlling the stepper motor used for cycling the filters into the agent optical path. The STEP signal on line 934 is input to the clock input of controller 940. When the signal changes state it clocks the controller. The DIR signal on line 936 is input to the direction input. The state of the DIR signal determines whether the stepper motor will turn clockwise or counter clockwise. The SRESET signal on line 938 is used to reset the controller at predetermined times. The output of controller 940 is the 4-line stepper motor control signal at 253.

The circuit shown at FIG. 8C is for generation of the gating and synchronization signals for demodulating the detected $CO_2$ and agent signals, and the generation and monitoring of the chopper motor drive voltage. The inputs to this circuitry are the timing signals from agent optical bench circuits 106 and the clock signals from the microprocessor.

The generation of the gating signals and synchronization signals for use in obtaining useful information from the detected gas and reference signals, will now be discussed. The AGENT TRACK signal on line 260 is the first input to differential receiver 1002. The second input on line 1003 is tied to ground. The output of differential receiver 1002 is input to pulse shaping circuit 1004. The second input is the CHOPCLK signal on line 808. The pulse shaping circuit processes the incoming signal so that clean pulses that are a CHOPCLK period wide are produced at its output. The output of pulse shaping circuit 1004 on line 1006 is input to the clear inputs of 4-bit counters 1008 and 1010. CHOPCLK signal on line 808 is input to the clock inputs of the counters.

The carry out output of counter 1008 is input to the enable inputs of counter 1010. There will be a continuous count until the counters are cleared. Hence, on the negative-going edge of the AGENT TRACK signal on line 260, which will be every 64 CHOPCLK pulses, the counters will be cleared.

Outputs of counter 1008 on lines 1012, 1014, 1016, and 1018, and the outputs of counter 1010 on lines 1022, 1024, 1026, and 1028, are input to PROM 1020. PROM 1020 is programmed for the waveform patterns for the AGENT SYNC, AGENT GATE, $CO_2$ SYNC, and $CO_2$ GATE signals. Therefore, based on the logic values of the signals output from the counters, PROM 1020 provides outputs to octal flip flop 1030 that will produce the programmed waveform patterns for these signals. When octal flip flop 1030 is clocked by the CHOPCLK signal, its outputs are the AGENT SYNC signal on line 570, the AGENT GATE signal on line 566. The $CO_2$ SYNC signal on line 564, and the $CO_2$ GATE signal on line 568.

The $CO_2$ TRACK signal on line 262 is input to differential receiver 1005. The second input on line 1003 is tied to ground. The outputs of differential receiver 1005 on line 1032 is input to frequency to voltage convertor 1046. The output of the convertor is the MTR SPEED signal on line 662 which is later converted to a digital signal and placed on the data bus and stored in memory.

The $CO_2$ TRACK signal output from differential receiver on line 1032 also is input to the phase input of phase comparator 1034. The second input to the phase comparator is the "Q4" output of 4-bit counter 1033. The data inputs of the counter are tied to ground and the CHOPCLK signal on line 808 is input to the clock input. The output at "Q4" will be the CHOPCLK signal divided by 16. The phase comparator is commercially available from RCA, Somerville, N.J. under model number CD4046B.

The output of the phase comparator on line 1036 is a voltage that is input to analog amplifier 1038. The output of the amplifier is the $V_{MOTOR}$ signal on line 1040 and the MOTOR RTN signal (ground) on line 1042. These signals drive the chopper motor.

If the frequency of the $CO_2$ TRACK signal on line 1032 falls outside a predetermined window when compared to the CHOPCLK signal divided by 16, the LOST signal on line 1044 will change state, clocking flip flop 922 (FIG. 8B) and changing the state of the LOST' signal that is output from the flip flop on line 926. This signal is put on the data bus to indicate to the microprocessor that the chopper motor signal is not what it should be and can cause system shut down.

The FILTER HOME signal on line 256 from the agent optical bench is input to invertor 1050 where it is squared up. The output of the buffer is the FILTER HOME' signal on line 932 that is put on the data bus to indicate to the microprocessor when the reference filter is in the agent gas optical path.

Operation

The general operation of the agent gas analyzer of the present invention will now be described. A detailed discussion will follow in the software implementation section.

The agent gas analyzer of the present invention is a single channel, four wavelength infrared filter photometer. The agent gas filter wheel rapidly switches each of the four filters into the agent gas optical pathway so that four specific wavelengths of infrared light are caused to issue on a detector. Since each anesthetic gas of interest, halothane, enflurane, and isoflurane, has a unique absorption spectrum in the infrared, the change in the infrared light intensity in each filter bandwidth is a measure of absorption, and thus the concentration of each agent gas. These gas concentrations are determined for both the inspired and expired breath phases.

Three of the four filters transmit narrow bands of infrared light that are used to analyze the absorption by the agent gases. The relative absorption of the respiratory gas being sampled at these narrow bandwidths provide a gas concentration measurement for the three agent gases using multi-parameter analysis. The fourth filter is a reference filter that transmits infrared light at a narrow bandwidth that is not absorbed by the gases of interest; it, therefore, provides a reference value for making the measurements with the other three filters.

The agent gas analyzer of the present invention has two basic operating modes: I/E (inspired/expired) mode and averaging mode (which is also referred to as the verifing mode). The agent gas analyzer normally operates in the I/E mode unless there is a special condition, then it operates in the averaging mode.

In the I/E mode, the object is to measure as rapidly as possible the absorption in the narrow bandwidths of the three filters. The signals that are detected are used collectively to determine the specific agent gas type and concentration using third order analysis.

In order to conduct this type of analysis, it is necessary for there to be at least the same number of filters as the gases for which you want to determine the concentrations. With this requirement satisfied, during each phase, inspired and expired, there is always an attempt to cycle at least three filters into the agent gas optical path. If this can be done, then the three filter measurements are used to calculate the concentrations for the agent gases. This cycling of filter elements and calculations of gas concentrations is performed separately for the inspired and expired phases of a breath.

Breathing is dynamic, therefore, there is no guarantee that the length of an inspired or expired breath phase, that would allow accurate measurement, will be long enough to cycle the three filters through the agent optical path. During the times when the three filters can not be cycled through the agent gas optical path, the value for the missing one or two filters is interpolated using the value for such filters before and after the event in which there was not time for a particular filter value determination. In interpolating a filter value that is missing, a time-weighted average is made of the last measurement for that filter and the next measurement. The concentration for the breath including at least one interpolated value is reported as soon as there is a three filter value set to calculate concentrations.

Depending on whether there was one or two filters which could not be cycled during a particular breath phase, there may be a one or two breath delay before the next agent gas concentrations are calculated. Table 1 shows representative examples of the interpolation and reporting for breath phases of durations that allow cycling of one, two, or three filters.

TABLE 1

Breath Phase Map: 1 Filter Steady State

TABLE 1-continued

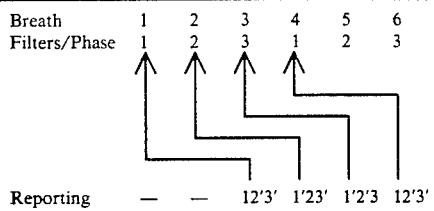

Breath Phases Map: 2 Filters Steady State

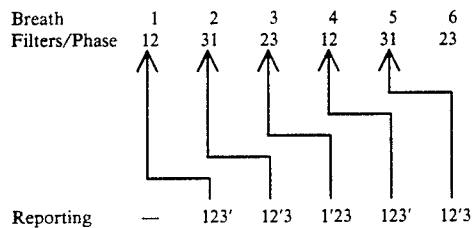

Breath Phase Map: 3 Filters to 1 Filter (Transitions at 2)

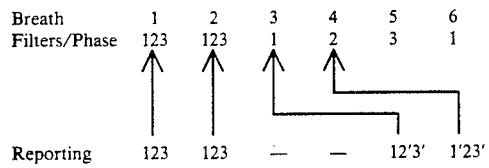

Breath Phase Map: 3 Filters to 2 Filters (Transitions at 2)

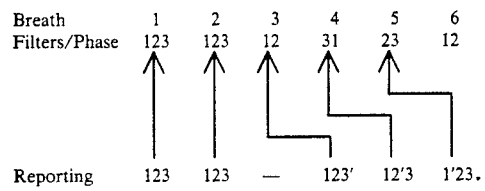

Breath Phase Map: 1 Filter to 3 Filters (Transitions at 3)

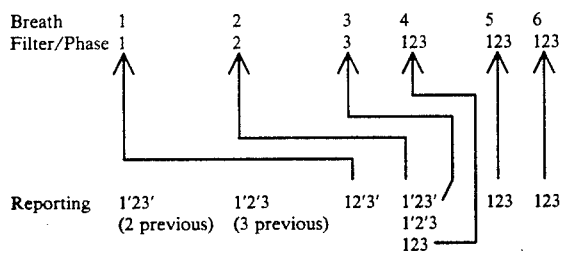

Breath Phase Map: 1 Filter to 2 Filters (Transitions at 3)

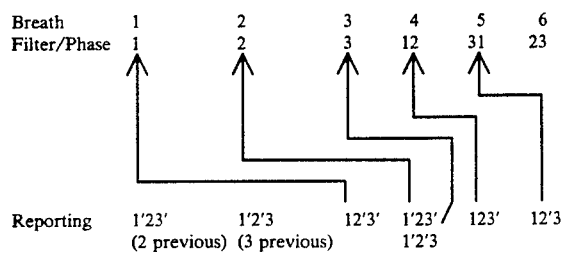

Breath Phase Map: 2 Filters to 1 Filter (Transitions at 3)

TABLE 1-continued

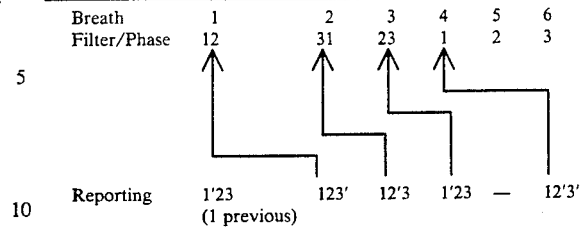

Breath Phase Map: 2 Filters to 3 Filters (Transitions at 3)

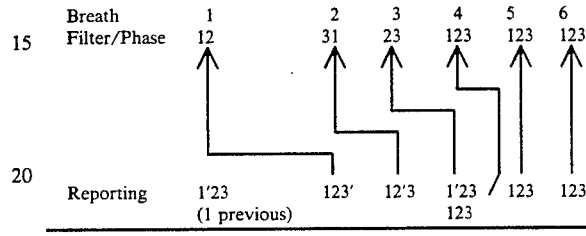

The filters with the prime next to it, for example, "3'," indicates that it is an interpolation. The dashed lines indicate that no calculation was made at the end of that particular phase. The lines from the reported interpolated value to the Filter/Phase line is to indicate the breath being reported.

To determine when either the inspired or expired phase is proper for making filter measurements, a running least-squares fit of multiple data points is used. When the least-squares slope is in a predetermined range, filter measurements can be made. It is understood that other slope determining methods may be used and still be within the scope of the present invention.

The second mode of operation is the averaging mode. This may be used in a number of special cases, for example, there is no $CO_2$ waveform, during calibration with a fixed gas, during very high breath rates, or when there is an erratic breath pattern. In this mode, the filters are cycled sequentially at a predetermined time interval. During this time, the reference filter is cycled on a non-interfering basis.

To determine the average value for each filter, the maximum and minimum measured values for that filter are determined. The natural log of each maximum and minimum is calculated, then the natural logs are arithmetically averaged to determine the filter value. It is to be understood that other methods of processing the data may be used.

The agent gas concentrations are calculated by using the averaged filter values. As each successive average is made, it is combined with the two immediately prior filter values for calculation of the agent gas concentration. Table 2 shows reporting of filters under the averaging method.

TABLE 2

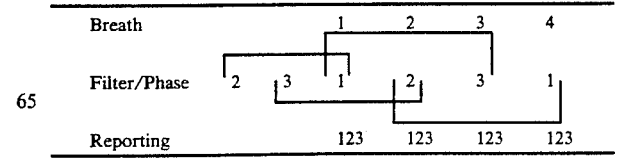

Software Implementation

FIG. 9 to 18 will be referred to in describing the software. In describing those figures, reference will be made to data lines and control lines. These references are not meant to be interpreted as hardwire connections that have been referred to in describing the circuits associated with the apparatus of the invention, but are illustrative of data flow.

The software operates the hardware so that real-time concentrations of the constituent gases, which in this case are halothane, enflurane, and isoflurane, are provided.

The operating system software of the agent analyzer is a multi-tasking system with timer management and local event flags. The multi-tasking supports two levels of priority, and time slicing among tasks of the same priority. Events of higher priority are always executed first. Generally, processes involving device I/O or communication execute at the highest priority. All others are of a lower priority.

At start time, a software process may have an array of timers associated with it. Such a process may program any of its given timers to provide a trigger at specified times. The timers may be deactivated at any time.

Every process has 16 event flags. Fixed meanings are assigned some of these event flags, while others are available for use by the process during system operation.

The operating system software has the capability at system start-up to allow creation of processes that are to be used in the operation of the agent analyzer. It also has the capability during operation to allow for determination and deletion of unwanted processes. The conjunctive use of the multi-tasking, timers, time management, and event flags provide for tailored operation of the agent gas analyzer.

The software of the agent gas analyzer has an interprocesser communication system ("IPC") for handling message communications between processes, between the agent analyzer and an external apparatus, and between interrupt service routines ("ISRs") and processes. These communications allow, for example, reporting of process status, or instructions for starting or stopping processes. This message routing system is not limited to a "Yes"-"No" format by permitting dynamic, descriptive messages to be passed. The result is message communication between two peer processes within the communication domain of the software.

The function of the communication is to send and receive data packets and respond with an acknowledgement when they are received. The message protocol allows for normal transmission, receipt, and acknowledgement of messages, and check sums for a particular message. Messages are buffered before being sent and after they are received. Messages for transmission have included a destination CPU and process ID (PID), a source CPU and PID, a flag word and action word, and the address of a long message data buffer or short message data, packet length, and check sum.

There are three communications ISRs: input characters, transmit characters, and check control line transitions. The input ISR is activated when a message is received, the transmit ISR is activated when a message is to be sent, and the control line transition ISR monitors the status of CTS. When messages are to be received, if the receiver buffer is nearly full, the DTR bar output line is raised to inhibit the originator from sending. After retrieving a message from the receiver buffer, the DTR line is lowered, signaling readiness to receiver more messages. Hence, raising and lowering of the DTR bar line on one side causes an interrupt on the other side.

Figure 9:
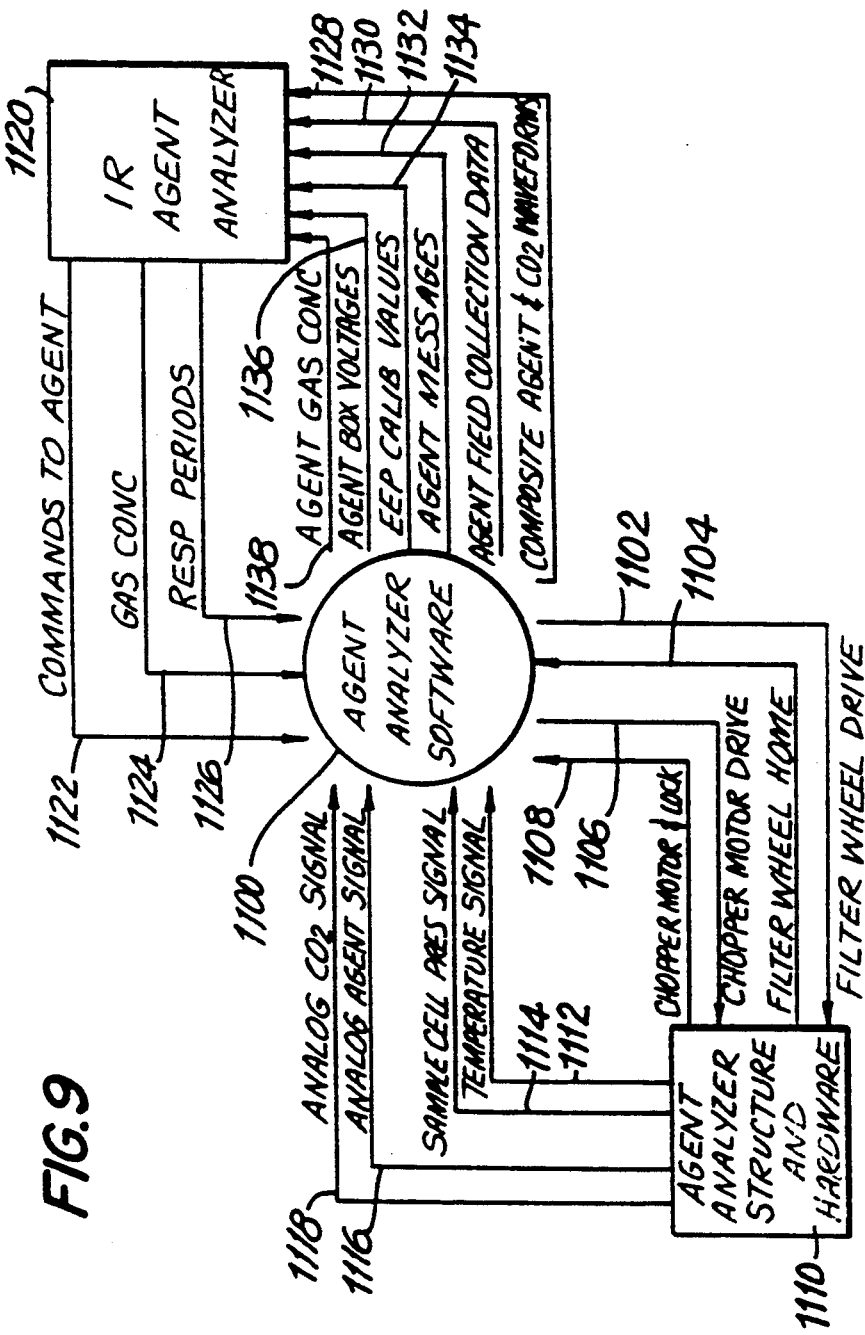
FIGS. 9-18 are the diagrams of the software for controlling operation of the agent gas analyzer of the present invention.

FIG. 9 is a context diagram of the agent gas analyzer software 1100 interfacing with agent gas analyzer structure and hardware 1110 and infrared gas analyzer 1120.

As shown, the agent analyzer software provides data on line 1102 to the agent gas analyzer structure and hardware for driving the filter wheel to specific filter position. The structure and hardware in return provides data on line 1104 which indicates when the filter wheel has positioned the reference filter in the agent optical path. As to a chopper wheel of agent analyzer, software 1100 provides data on data line 1106 for driving the chopper motor at a predetermined speed. The return data on data line 1108 is the monitor signals indicative of whether the actual chopper motor speed is synchronized.

Agent analyzer structure and hardware 1110 continuously provides data on line 1112 indicative of the measured temperature, the data on line 1114 indicative of the pressure in the gas pathway, the data on line 1116 indicative of the analog agent signal, and data on line 1118 indicative of the analog $CO_2$ signal.

The communication between agent gas analyzer and the infrared gas analyzer 1120 is peer to peer. Analyzer 1120 sends commands to the agent gas analyzer software on line 1122, data regarding certain gas concentration on line 1124, and data on respiratory periods on line 1126.

The commands that are sent are for the agent gas analyzer to perform its functions. Certain gas concentrations that are measured by analyzer 1120 are used by the agent gas analyzer in calculating agent gas concentrations. The respiratory periods are reported to give the agent gas analyzer a prior indication of the breathing rate before the gas stream reaches the agent section of the agent gas pathway.

The agent analyzer software provides the software of analyzer 1120 with agent gas concentration on line 1138, the agent analyzer voltages for temperature, pressure and other signals on line 1136, the EEPROM characterization values on line 1134, any agent analyzer messages on line 1132, the agent field collection data on line 1130, and the composite agent and $CO_2$ waveforms on line 1128. The agent field collection data is a collection of digital data regarding the agent and $CO_2$ gas, pressure and temperature as well as system statuses that are transmitted to analyzer 1120. These general descriptions of data flow for the agent analyzer software will be described in detail subsequently.

Figure 10:
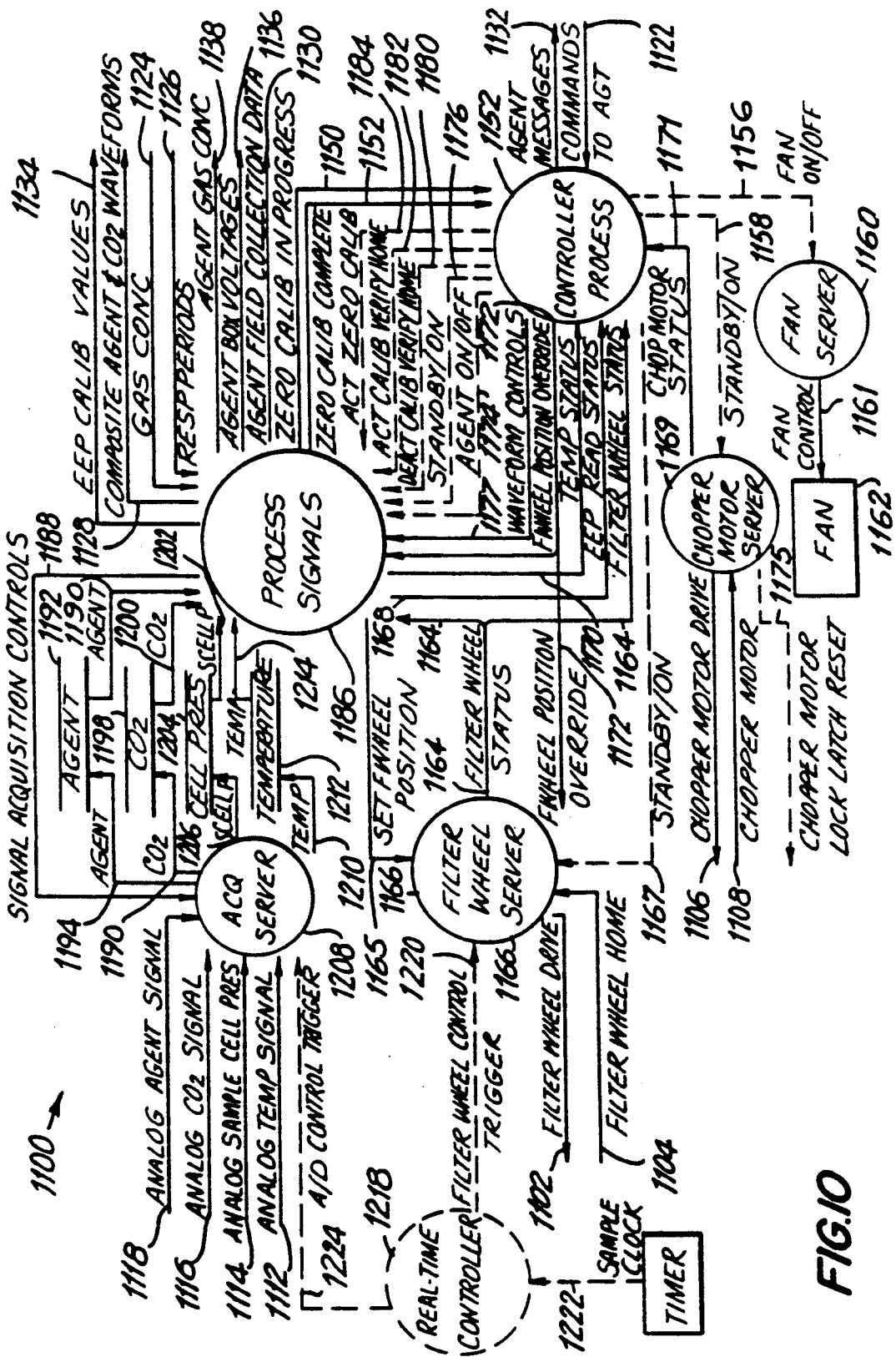

FIG. 10 is a detailed data flow diagram of agent analyzer software 1100 shown in FIG. 9. In FIG. 10, the solid lines are data flows, dashed lines are control flows, circles are software processes, squares are structure, and parallel lines are storage functions.

Referring to FIG. 10, the agent analyzer software has seven processes which can be run: acquisition server 1208, process signals 1186, controller 1152, filter wheel server 1166, chopper motor server 1169, fan server 1160, and real-time controller 1218.

Acquisition server 1208 receives the data lines 1112, 1114, 1116, and 1118 indicative of the analog signals from the agent optical bench for temperature, pressure, $CO_2$ gas, and agent gas, respectively. Also provided to acquisition server 1208 is the A/D control trigger control line 1224 from real-time controller 1218. Process signals process 1186, which runs the measurements tasks ("MTs") for calculating, among other things, the agent gas concentrations sends signal acquisition controls on data line 1188 to instruct the acquisition server 1208 what to measure. When the agent data A/D control trigger 1224 activates the acquisition server 1228, the agent data is sent via line 1194 to memory 1192. The data is retrieved from memory by process signals process 1186 via line 1190. The same takes place if $CO_2$, pressure, or temperature data is desired with the only difference being the data line and memory store used. In the case of $CO_2$, the data goes from the acquisition server to memory 1198 via line 1196, and then to the process signals via line 1190. For pressure, it is memory 1204 via line 1206 and to process signals 1186 via line 1202. And for temperature, it is to memory 1212 via line 1210 and process signals 1186 via line 1214.

The process signals carry out MTs. The data indicative of the measured analog signals are input to the process signals 1186 for use in calculating the agent gas concentrations.

With respect to filter wheel server 1166, process signals 1186 receives the filter wheel status data on line 1164 from the server. If the filter position must be changed, the process signals send a new filter position to the filter wheel server via data line 1165.

Controller process 1152 provides a number of controls to process signals 1186, and receives status signals from a number of processes. The controls are activate zero calibration on line 1184, activate the calibration verify mode on line 1182, deactivate the calibration verify mode on line 1180, the standby/on control on line 1176, and the agent MT on/off control on line 1174. Two additional data lines connect to the controller process which are the zero calibration in progress signal on line 1150 and the zero calibration complete signal on line 1152.

Status data that is provided are the EEPROM read status on line 1168, the temperature status on line 1170. The final lines between the controller and process signal process are the waveform controls on line 1177 and the filter wheel position override on line 1172.

Process signals process 1186 communicates with analyzer 1120 over all of the lines that connect analyzer 1120 and agent analyzer software 1100, except for the agent messages on line 1132 and the commands to agent analyzer on line 1122.

Controller process 1152 monitors the statuses and provides control signals to the rest of the software. This includes its connections to process signals process 1186. A function of the controller is to provide standby/on controls to other processes. The standby/on control on lines 1158 is to chopper motor server 1169, and the one on line 1167 to the filter wheel server 1166.

Since the temperature of the agent gas analyzer is controlled by activation and deactivation of the fan, fan on/off control on line 1156 is from controller process 1152 to fan server 1160. The controller process also receives status signals from chopper motor server and filter wheel server on lines 1171 and 1164, respectively. The final output from, and input to, the controller process is the previously described agent message data on line 1132 and commands to the agent analyzer on line 1122.

The connection to the filter wheel server have been described except for two. These final two are the filter wheel position override from the controller on line 1172. The second is the filter wheel control trigger on line 1220 which provides timing signals. The previously described filter wheel drive signal on line 1102 and filter wheel Home signal on line 1104 also connect to the filter wheel server.

The data lines and control lines to chopper motor server 1169 have been described except for one. The final line is the control, the chopper motor lock latch reset on line 1175.

Besides the previously described control lines to fan server 1160, the fan server provides the fan control data on line 1161 to the fan 1162 for driving it on or off.

All of the control lines from the real-time controller have been described except for one. The control line from the sample clock is input to the real-time controller on line 1222.

Now that the agent analyzer software has been discussed in general, each of the processes will be discussed in detail.

Acquisition server 1208 is for sampling the analog waveforms and providing the sampled values to the MTs of process signals 1186. 16-bit voltage samples are obtained by means of an A/D converter that is time-shared among all analog input signals.

The external interfaces to the acquisition server include an ISR that drives acquisition and the software that executes at a level of the process that requested the service.

Acquisition is accomplished by use of signals and streams. A stream may be opened, closed, or controlled. Stream control will involve, for example, programming sample interval and a sample start time. A signal is a particular channel and has characteristics associated with the A/D system itself. For example, signal characteristics may involve programming the system offset or gain. A process that has opened a sampled signal stream will begin to receive an inflow of samples at regular intervals. Sample stream messages are of two types: buffered and unbuffered. Unbuffered is real-time. Buffered involves a delay and is used when it is desired to obtain a number of samples at once in a particular time interval. In the time interval, the acquisition process will fire, and proceed to service the list of stream descriptors. A stream descriptor is allocated on behalf of requesting process whenever it issues a successful stream open. These descriptors are different for each signal and stream.

Figure 11:
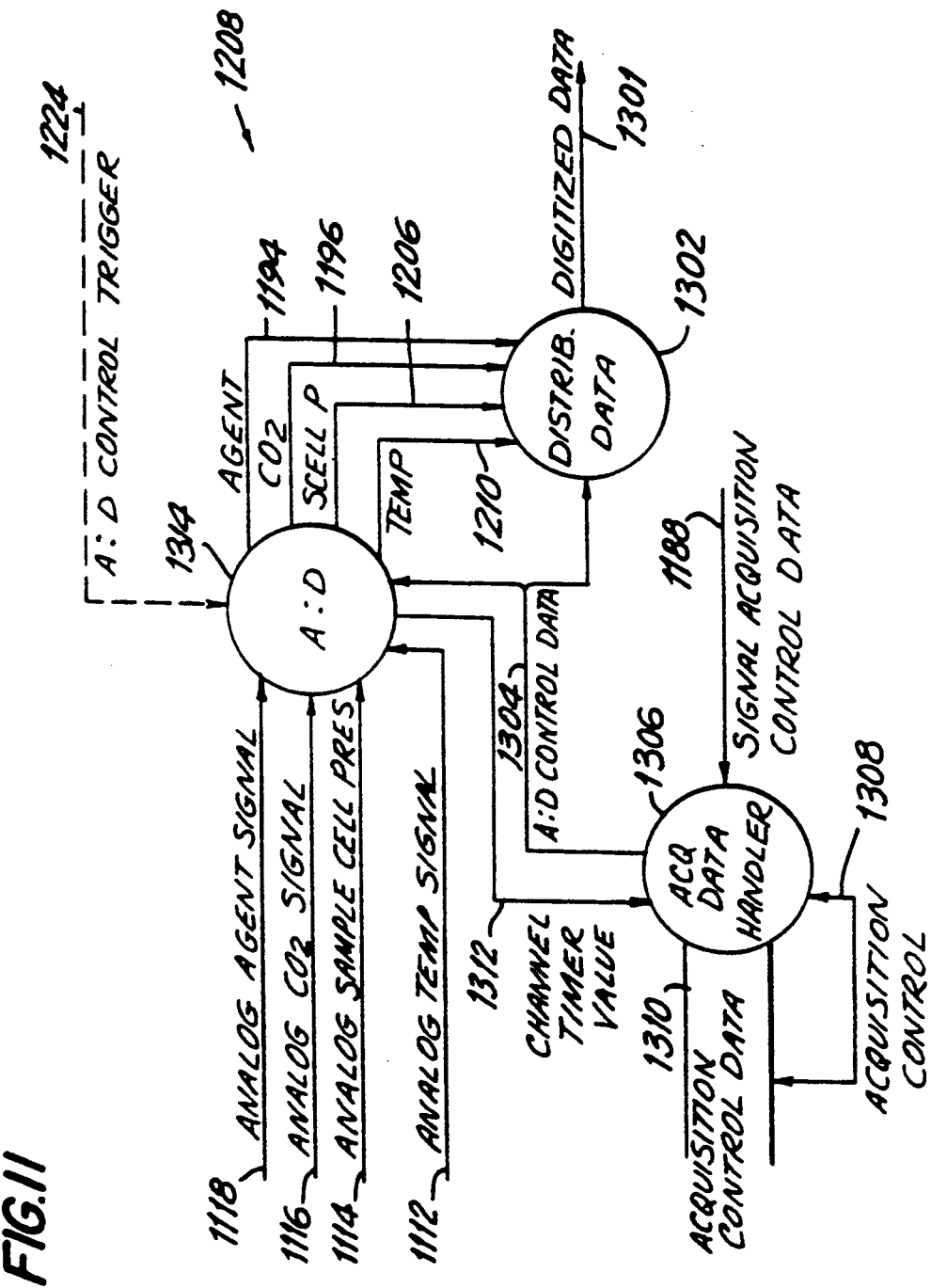

Referring to FIG. 11, acquisition server 1208 will be described. The subprocesses of the acquisition server are A/D process 1314, distribute data process 1302, and acquisition data handling 1306.

The analog signals are input to the A/D process 1314 on data lines 1112, 1114, 1116, and 1118 which are the analog signals for temperature, pressure, $CO_2$ gas, and agent gas, respectively. When the A/D control trigger control is active, data conversion takes place.

Acquisition data handler process 1306 selects via acquisition control data line 1308 from memory at 1310 the acquisition control data stream and signals that are to be used. This selection is based on the MTs that are being run by process signals process 1186 and the instructions which are supplied to the handler via acquisition control data on line 1188 from the process signals process. The final input is the channel time value data on line 1312 which is used by the acquisition handler to determine which streams are sampled, if any.

The A/D control data on line 1304 is sent to A/D process 1314 and distribute data process 1302. The data on line 1304 is the stream and signals to be sampled, and how the data is to be distributed i.e., buffered or unbuffered. The distribute data process will distribute the converted data it receives from the A/D process, which is the agent data on line 1194, $CO_2$ data on line 1196, pressure data on line 1206, and temperature data on line 1210. In the distribution data process packages the data and provides it on line 1301 to process signals process 1186.

Figure 12:
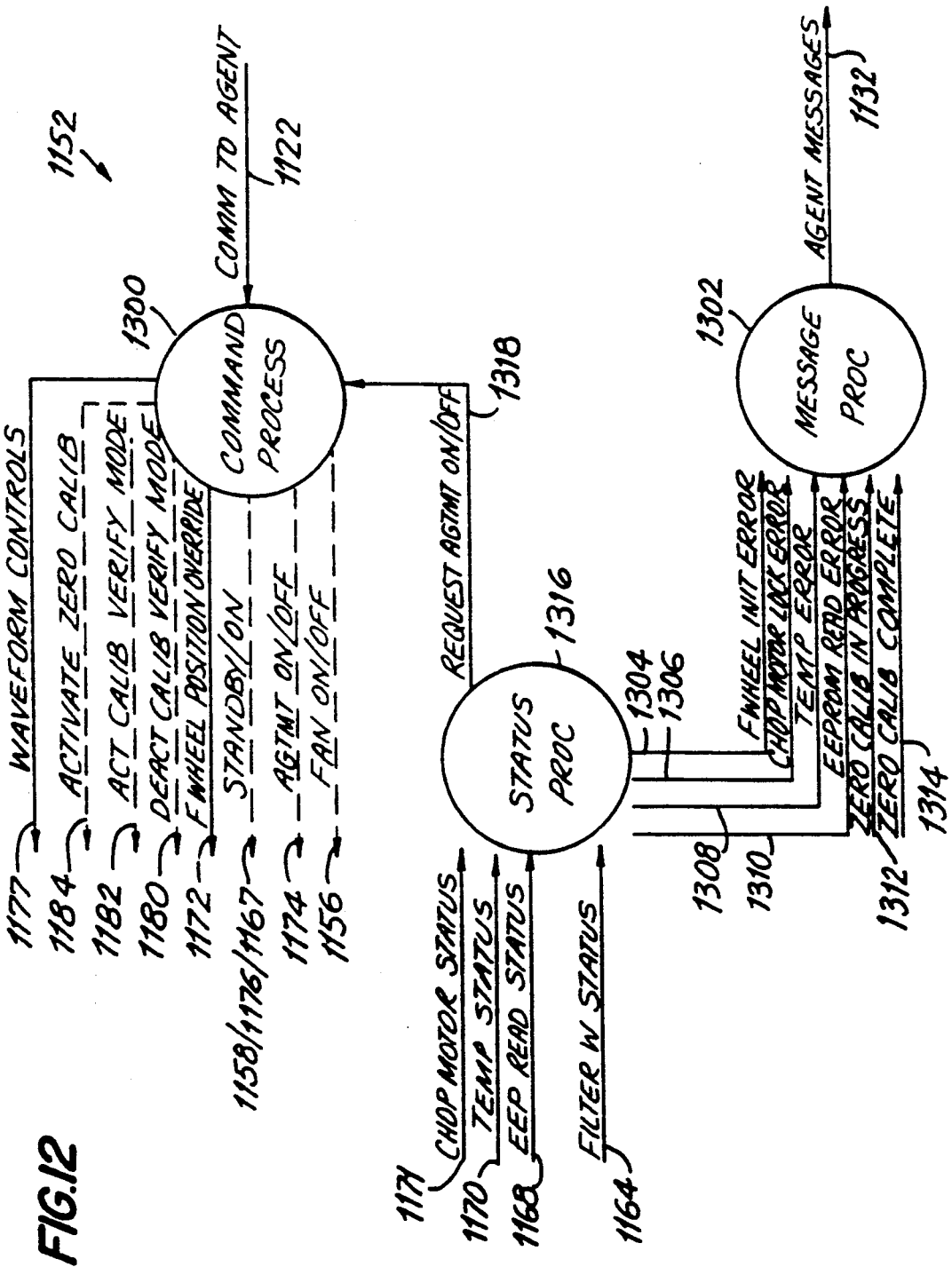

Controller process 1152 is shown in detail in FIG. 12. The controller is the supervising process for all processes of the agent gas analyzer. Once the system is operational, the controller communicates with analyzer 1120. The controller is responsible for changes implementing changes in operating mode, and starting and stopping certain processes.

The controller process receives all of the commands from analyzer 1120 on data line 1122. These are evaluated by the command process 1300. These commands may generate controls to the agent MT of the process signals process such as activate zero calibration of the agent channel, activate or deactivate the calibration verify mode, placing the testing MT in standby or on, or activating or deactivating the agent measuring task, and the control for activating or deactivating the fan. The commands may also be waveform control data to be sent to the waveform server of the process signals process or data to be sent to the filter wheel server to the filter wheel position override.

Status process 1316 receives the chopper motor status on line 1171, the temperature status on line 1170, the EEPROM read status on line 1168, and the filter wheel status on line 1164. It processes these signals and generates the request Agtmt on/off on data line 1318 and the error messages which are sent to message process 1302. The error message may be the filter wheel initialization error on line 1304, the chopper motor lock error on line 1306. The temperature error on line 1308, or the EEPROM read error on line 1310. The two other data lines to message process 1302 are the zero calibration in progress data on line 1312 and the zero calibration complete on line 1314. The message process processes all of the data and sends agent messages to analyzer 1120 on line 1132.

Figure 13:
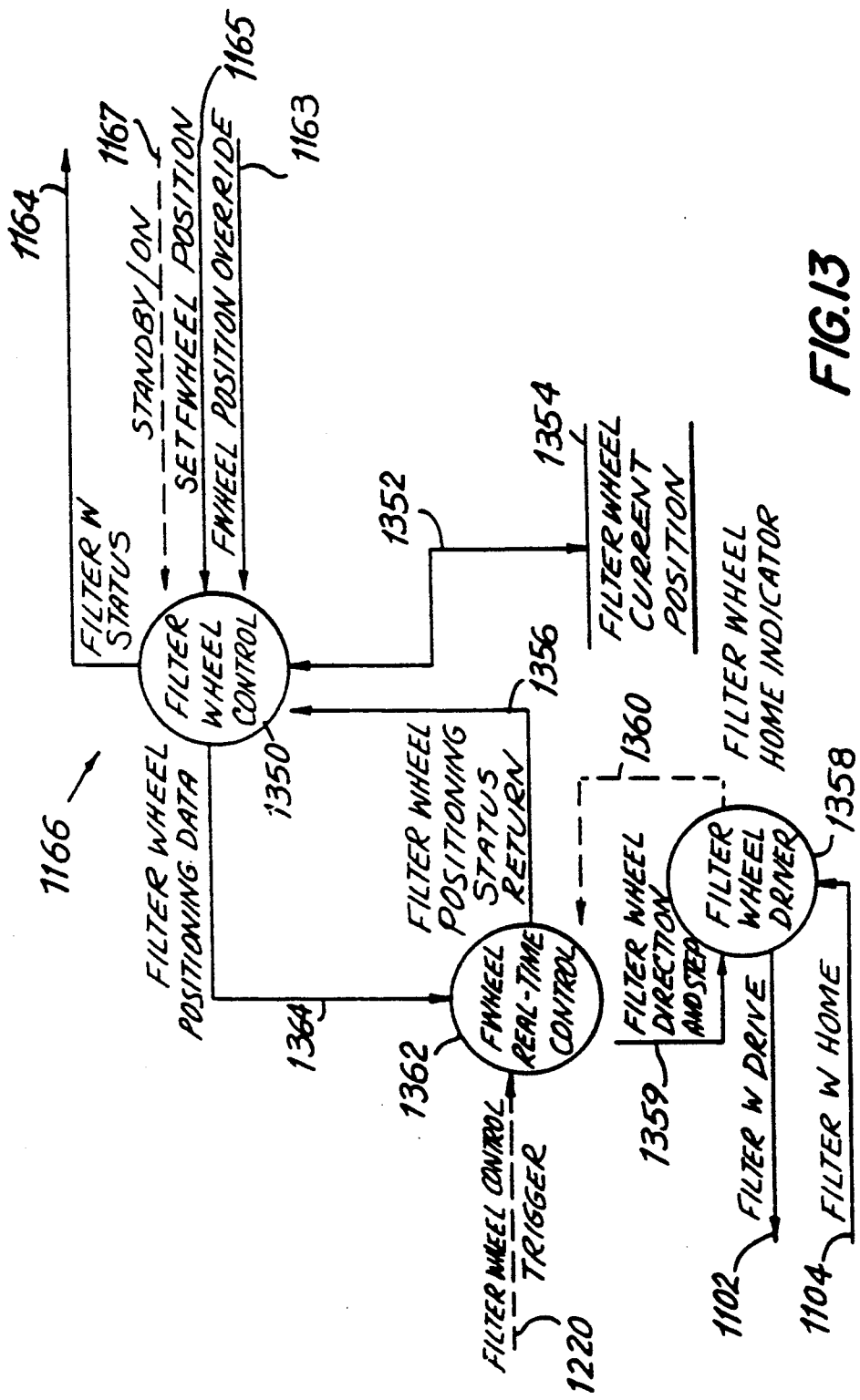

FIG. 13 is a detailed flow diagram of filter wheel process server 1166. The filter wheel server process enables internal and external processes to control the position of the filter wheel. The filter wheel server process responds to command message transmitted through the IPC subscription, performs the requested operations and responds with an operation completion status message.

The filter wheel server has the subprocesses filter wheel control process 1350, filter Wheel real-time control processes 1362, and filter wheel driver 1358. The data for setting the filter wheel position is sent from the agent MT of the process signals process. This will be acted upon unless the control on line 1167 places it in standby or there is filter wheel position override data from analyzer 1120 on line 1163.

When new position data is received, the current filter wheel position stored in memory 1354 is read via data line 1352. If it is the same, this memory will not be changed; however, if it is different it will be changed to the new position when the filter is moved.

The new filter wheel position data is sent on line 1364 to filter wheel real-time control process 1362. Once the real-time trigger signal, is received by this process, the direction and stop data are sent to filter wheel driver process 1358 on data line 1359. The driver process Will send the direction and stepping data to the stepper motor on line 1102.

If it is being stepped and the reference filter passes through the agent optical path, feedback is provided to drive process 1358 on line 1104. The drive process provides a control on line 1360 to indicate when the reference filter has been in the agent optical path.

Once the filter has been moved to the new position, real-time control process 1362 will return the positioning status on line 1356 to filter Wheel control process. Data line 1164 returns the filter wheel status to process signals process 1186 and the controller 1152. The filter Wheel server process Will now wait for the next instruction for movement of the filter wheel.

Figure 14:
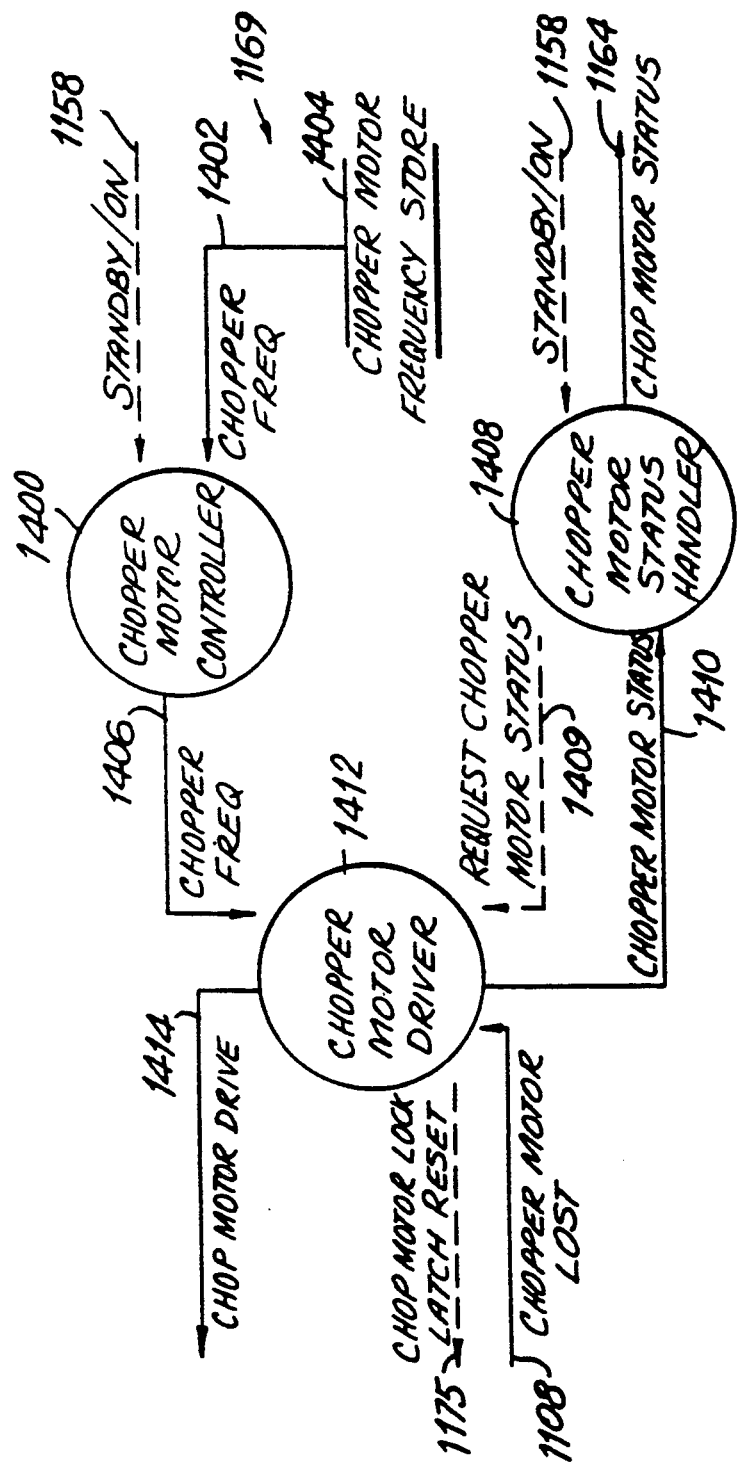

FIG. 14 shows chopper motor server process 1166 in greater detail than is shown in FIG. 10. The chopper motor server process includes three subprocesses: chopper motor controller process 1400, chopper motor driver process 1412, and chopper motor status handler process 1408.

The programmed chopper motor frequency is stored in memory 1404. When via control line 1158, the chopper motor controller process is activated, the programmed frequency is retrieved on line 1402 from memory 1404. The chopper frequency is sent to the chopper motor driver process on data line 1406.

Based on the chopper frequency, the chopper motor driver process generates signals to drive the chopper motor on line 1414. The motor speed is monitored and if it is above or below a predetermined threshold, it will indicate it to the chopper motor driver process on data line 1108.

On a timed basis, the chopper motor status handler process 1408 requests chopper motor status from the chopper motor drive process via control line 1409. In response to the requests the status is reported on line 1410. The handler inputs the status to controller process 1152.

Figure 15:
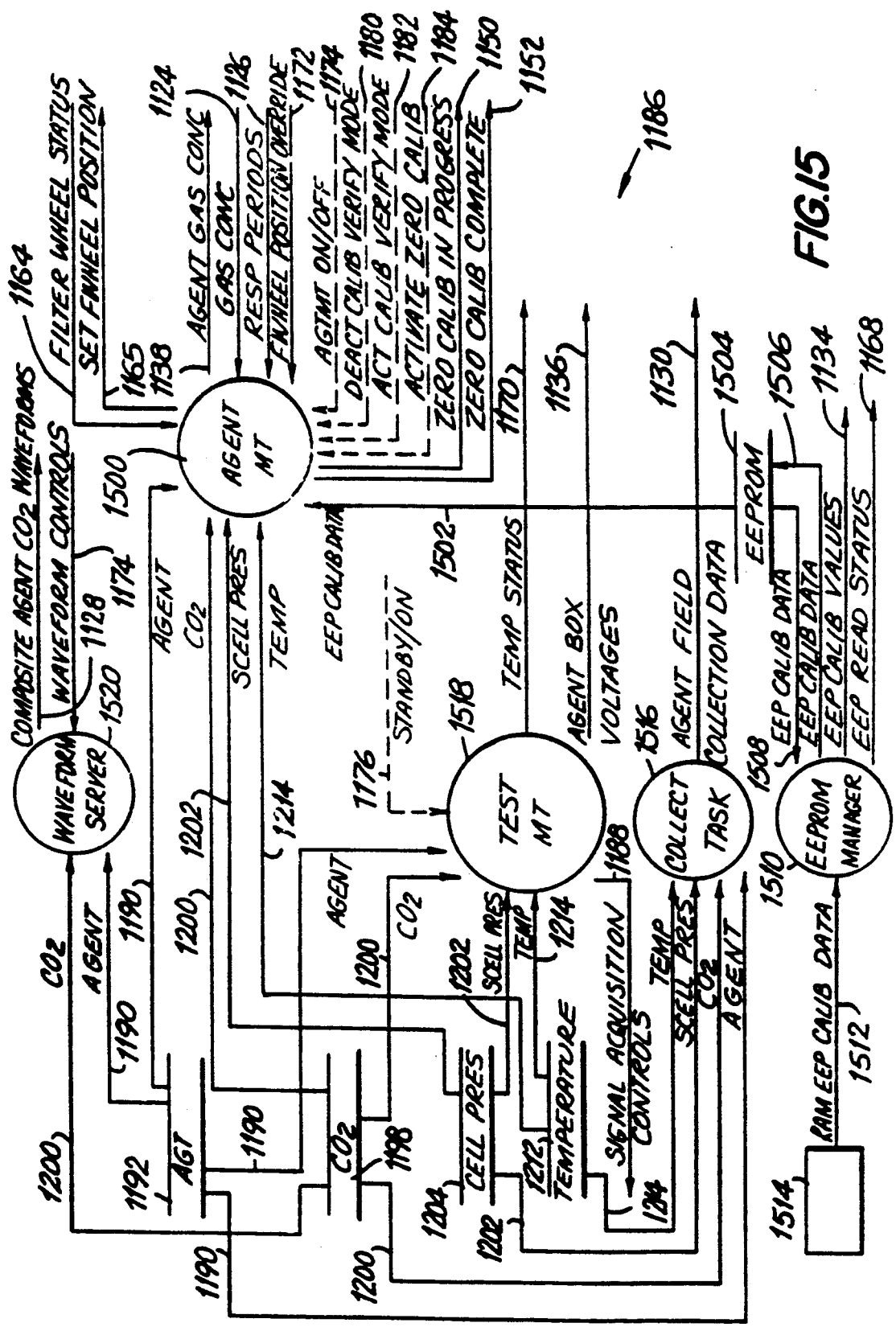
Figure 16:
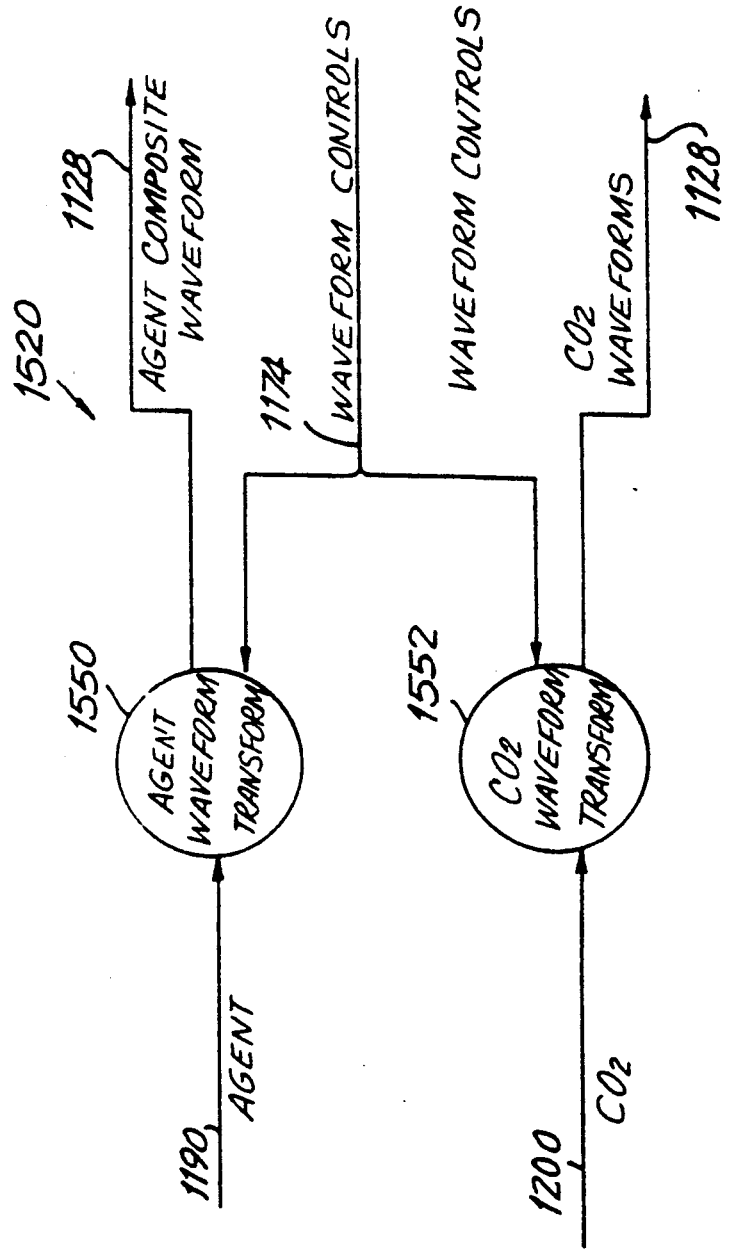
Figure 17:
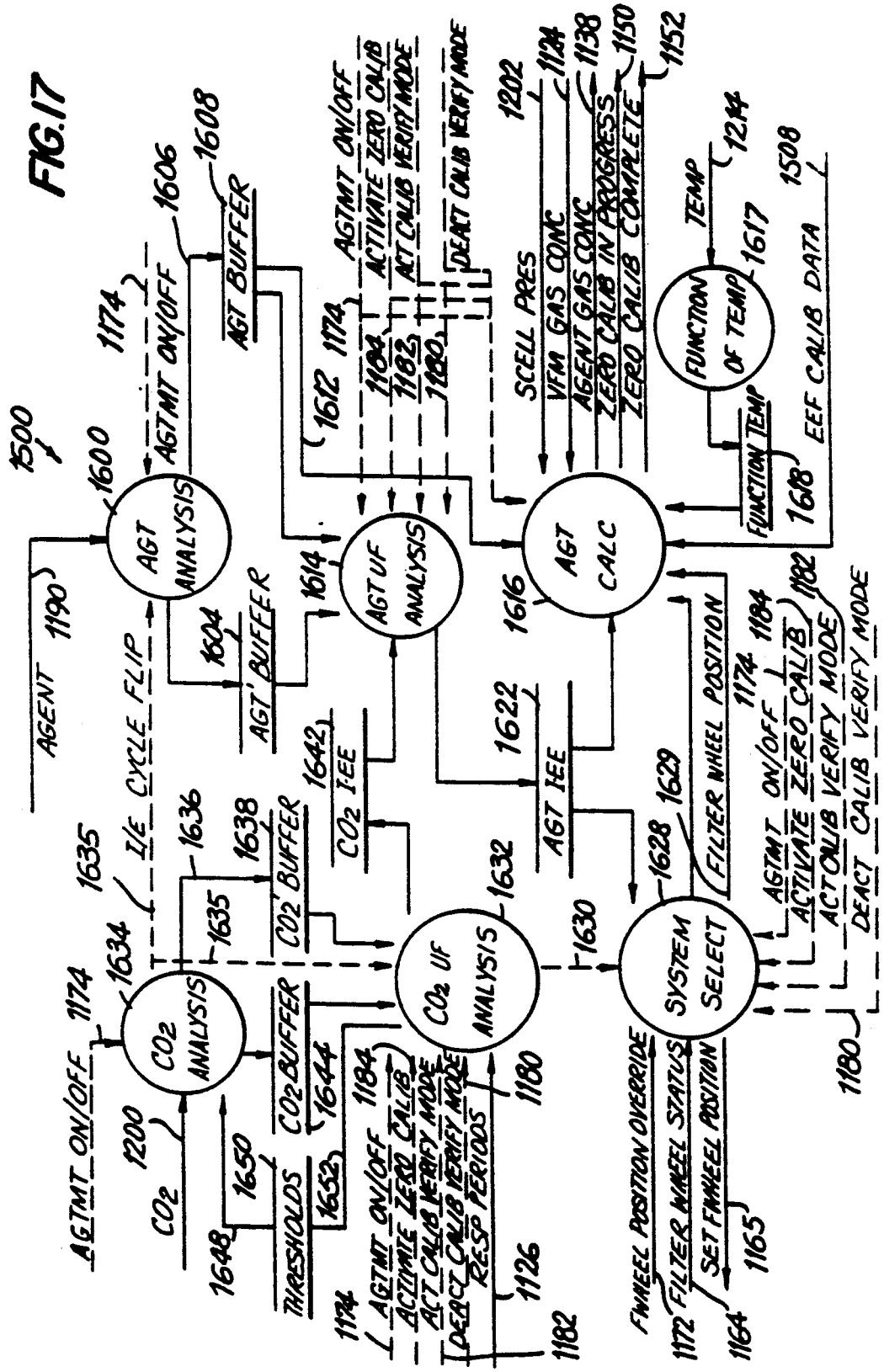
Figure 18:
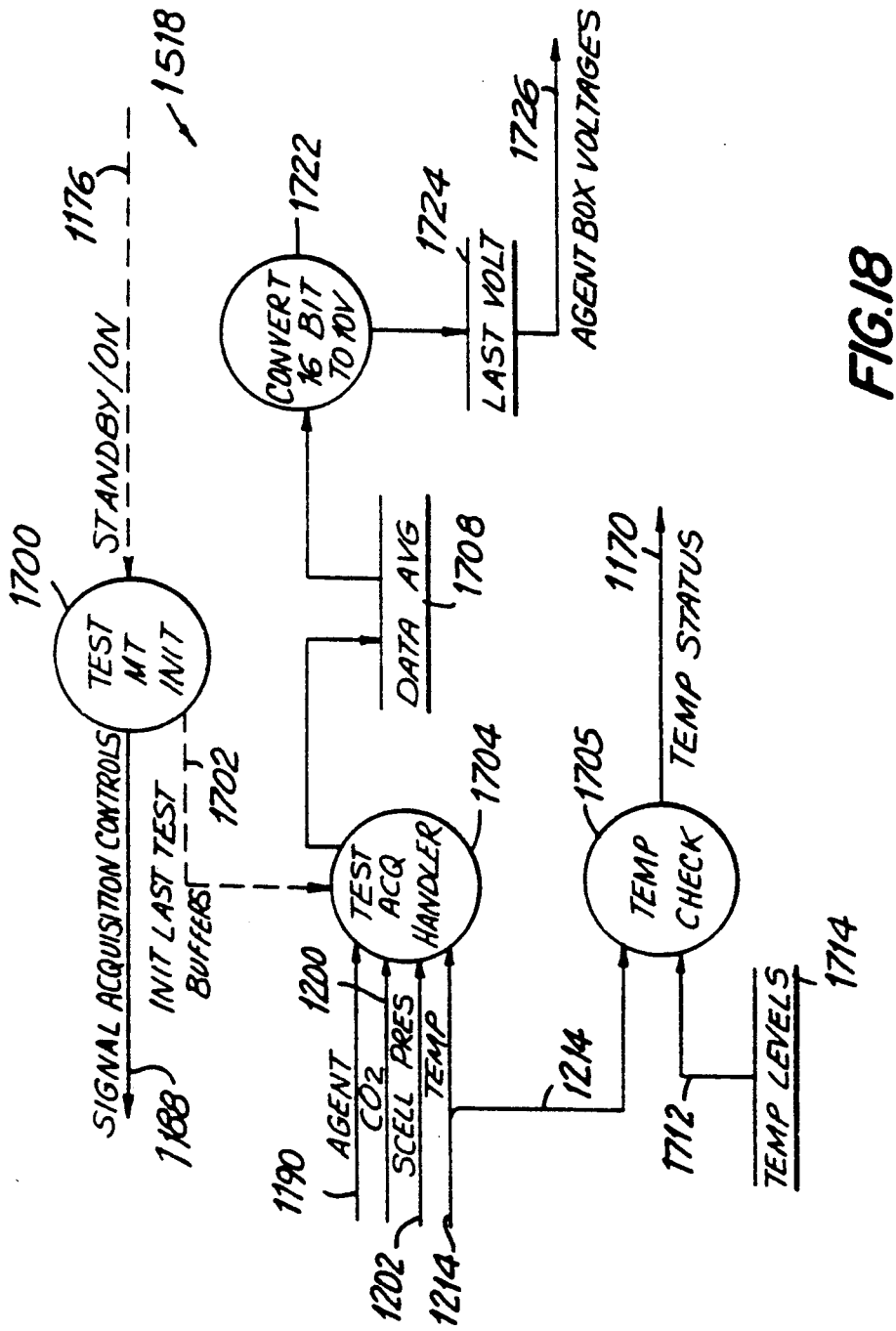

FIG. 15-18 are a detailed data flow diagrams of process signals process 1186. FIG. 15 shows the process signals process, FIG. 16 shows waveform server process 1520 in greater detail, FIG. 17 shows agent MT process 1500 in greater detail, and FIG. 18 shows test MT process in greater detail.

Referring to FIG. 15, the process signals process has five subprocesses. These are waveform server process 1520, agent MT process 1500, test MT process 1518, collect task process 1516, and EEPROM management process 1510. Process signals process 1186, when requested, performs all of the MTs for the agent gas analyzer.

Referring to FIG. 15 and 16, waveform server process 1520 will be discussed. The waveform server has two subprocess: agent waveform transformation process 1550 and $CO_2$ waveform transformation process 1552. These transformation processes are for the agent data on data line 1190 and the $CO_2$ data on data line 1200, respectively.

When a command, for example, from analyzer 1120 is provided for one or both waveforms on line 1174, the transformation processes are activated appropriately to transform the agent or $CO_2$ data to waveforms. Upon completion of the transformation, the $CO_2$ waveform data and the agent composite waveforms are sent on data line 1128 to analyzer 1120.

Referring to FIGS. 15 and 17, agent MT process 1500 will be described. The agent MT process has seven subprocesses. These are agent analysis process 1600, $CO_2$ analysis process 1634, agents waveform analysis process 1614, $CO_2$ waveform analysis process 1632, agent calculation process 1616, filter select process 1628, and function of temperature process 1617.

The $CO_2$ data on line 1200 is input to $CO_2$ analysis process 1634. This process analyses the $CO_2$ data for inspired and expired breath events. This decision is made by determining if certain thresholds have been crossed. These thresholds are stored in memory 1650 and provided to $CO_2$ analysis process 1634 on data line 1648. These thresholds are continuously adjusted by the $CO_2$ waveform analysis process 1632 to conform to the waveform size. As the thresholds are changed, they are stored in memory 1650 via data line 1652.

The $CO_2$ data that is analyzed by $CO_2$ analysis process is buffered in memories 1644 and 1638, which are a $CO_2$ data and a rate of change buffer, respectively. The data is there for the $CO_2$ waveform analysis process 1632 to retrieve. The respiratory periods on line 1126 measured by analyzer 1120 are also provided to the $CO_2$ waveform analysis process to aid in its waveform analysis.

The $CO_2$ analysis process provides the I/E cycle changes for inspired and expired breath phases on control line 1635 to agent analysis process 1600 and to $CO_2$ waveform analysis 1632. In supplying it to the $CO_2$ waveform analysis process, the phases can be matched with the detailed waveform analysis being preformed to determine the plateau at which the gas is stable. This data is used in making calculations for the separate phases which is based on the thresholds provided by the $CO_2$ waveform analysis process. The $CO_2$ inspired and expired plateau information that was determined by $CO_2$ waveform analysis process 1632 is stored in memory 1642. The $CO_2$ waveform analysis on control line 1630 provides filter select process 1628 the plateau control information.

The agent data on line 1190 is processed by agent analysis process 1600. The agent data and rate of change data are buffered in memories 1604 and 1608, respectively. The buffered data is provided to agent waveform analysis process 1614. Based on the times when the $CO_2$ had an inspired or expired plateau (from memory 1642) and additional agent rate of change criteria, the process will determine the plateaus from the agent data which is stored in memory 1622.

The times when the agent has plateaus is retrieved by filter select process 1628 and agent calculation process 1616. The filter select process will move the filters during the plateau periods. It will also inform the agent calculation process which filter is in the agent optical path based on the filter wheel status.

The parameters that are needed to make the agent concentration calculations are provided to agent calculation processes according to the equations set forth subsequently.

Function of temperature process 1617 calculates the effect of temperature on pressure which is then stored in memory 1618. This is retrieved by the agent calculation process when needed.

It may be desired to operate the system in the verify mode in which the inspired and expired phases are ignored and the filters are cycled and agent calculations are made. Further, the agent MT may be operated to make zero gas calculations.

In the operation of the agent MT, in order to make the required measurements, a running 10-point least-squares fit is performed on the incoming $CO_2$ and agent data. The results of this analysis will be a running real-time slope for the $CO_2$ and agent data, and a running average for the agent data.

Three criteria must be satisfied before data from a particular filter may be qualified for use. These criteria are: (1) the $CO_2$ signal must be determined to be in an inspired or expired phase of a breath cycle as determined by the signal crossing of a predetermined threshold, (2) the slope of the $CO_2$ signal must be within a predetermined range, and (3) the slope of the agent signal must also be within a predetermined range. Once these three criteria are met, the averaged agent data is used for agent gas calculations.

Referring to FIGS. 15 and 18, test MT process 1518 will be described. The process has four subprocesses: test MT initialization process 1700, test acquisition handler process 1704, and test check process 1705, and convert 16-bit to 10 V process 1722.

The purpose of the test MT process is to generate voltages for the measured agent, $CO_2$, pressure, and temperature signals, and to check temperature status.

When the test MT initialization process is started, it sends data on data line 1188 to the acquisition server process to acquire signals. In response, data is input to test acquisition handler process 1704 for the agent, $CO_2$, pressure, and temperature. The signal on control line 1702 indicates to the handler process that new data is coming.

The test acquisition handler averages the data and stores it in memory 1708. The stored data is then converted and stored in memory 1724. The agent box voltages are sent to analyzer 1120.

The temperature signal is sent to temperature check process 1205 which evaluates if it is within the temperature range stored in memory 1714. This evaluation is then sent to the controller on data line 1170.

The remaining two processes to be discussed are collect task process 1516 and EEPROM management process 1510. The collect task process collects the measured values for temperature, pressure, $CO_2$ and agent, and supplies them on a single data line 1130 to analyzer 1120 along with other system status information.

The EEPROM management process receives data for use in agent concentration calculations from EEPROM 1514. The EEPROM management process transforms this data and stores it in memory 1504 via data line 1506. This EEPROM management process outputs to analyzer 1120 on data line 1134 the EEPROM values, and outputs to controller 1152 the status which indicates if there are any read errors.

Agent Gas Concentration Calculation

The primary function of microprocessor 806 is to calculate the partial pressures or concentrations of the plurality of agent gases in a respiratory gas stream. In calculating the concentrations, the microprocessor corrects for nitrous oxide in the agent channel, pressure in the agent gas pathway, temperature in the agent optical bench, and characterization.

Characterization coefficients for the agent gas analyzer are based on the fact that a manufacturer constructs each agent analyzer of a particular type with the same components; however, corresponding components in two different analyzers may have different responses. The result is that two different agent analyzers making partial pressure measurements can derive two different values even though both are operating properly.

Accordingly, each agent analyzer has its own specific characterization coefficients. These coefficients are stored in EEPROM 450. Hence, the application of each agent analyzer's characterization coefficients to raw measurements of a known gas standard bring about the same result. This result is consistent with industry standards and made without any calibration to the bench's components. The other values stored in the EEPROM 450 are the temperature transducer voltage at the reference temperature, the nitrous oxide correction coefficients, the span factor and offset for correcting pressure measurements, zero gas vector, calibration number, and serial number of the agent analyzer optical bench.

The calculations for the concentrations of the plurality of agent gases in the respiratory gas stream will now be discussed.

The signals that are provided for real-time calculation of these agent gases, halothane, enflurane, and isoflurane, are the agent gas signals that were detected, the pressure in the gas pathway at the pressure transducer, and the temperature of the agent optical bench. In making readings at the agent optical bench, the filter wheel may place one of four filters in the agent optical path. This is the reference filter or one of the three measurement filters.

The first step in determining the concentration of the agent gases is to make the absorption calculation. To determine this, the ratios and scale factors for the measurement filters must be calculated. The ratios are determined according to the following expression:

$$R_j = \frac{V(Agt)_j - V(Agt)_{ofs}}{V(Agt)_0 - V(Agt)_{ofs}} \quad (1)$$

where, $V(Agt)_j$ = the measured agent voltage for filter 1, 2 or 3.
$V(Agt)_0$ = the measured agent voltage for the reference filter.
$V(Agt)_{ofs}$ = the measured offset voltage for the agent channel.
j = the filter index variable: 1, 2, or 3.

The scale factors are determined by the following expression:

$$S_j = \frac{V(Agt)_{zj} - V(Agt)_{ofs}}{V(Agt)_{z0} - V(Agt)_{ofs}} \quad (2)$$

where, $V(Agt)_{zj}$ = the measured agent voltage with zero calibration gas in the gas pathway for filter 1, 2, or 3.
$V(Agt)_{z0}$ = the measured agent voltage with zero gas for the reference filter.
$V(Agt)_{ofs}$ = the measured offset voltage for the agent channel.

After determining the ratios and scale factors, the absorption vector is determined by the following expression:

$$A_j = -\ln\left(\frac{[R_j]}{[S_j]}\right) \quad (3)$$

where, $-\ln[\ ]$ = minus the natural log of the ratio within the brackets.

$R_j$ = the ratio for filter 1, 2, or 3.
$S_j$ = the scale factor for filter 1, 2, or 3.
j = the filter index variable: 1, 2, or 3.

The absorption vector must now be corrected for nitrous oxide. The pressure of nitrous oxide in the agent gas pathway is determined by the following the expressions:

$$P_{CELL} = (V(Prs)(PrsSpn)) + PrsOfs \quad (4)$$

where, $P_{CELL}$ = the agent gas pathway pressure in mmHg.
V(Prs) = the measured pressure at the pressure transducer.
PrsSpn = pressure transducer span factor stored in EEPROM 450.
PrsOfs = pressure transducer offset stored in EEPROM 450.

$$P_{N20} = \frac{(\% \ N20_{EXT})}{(100)} (P_{CELL}) \frac{(RefTmp \ V)}{(V(Tmp))} \quad (5)$$

where, $P_{N20}$ = the partial pressure of nitrous oxide in the agent gas pathway.
%$N20_{EXT}$ = inspired and end-tidal nitrous oxide concentration from an external source.
$P_{CELL}$ = the agent gas pathway pressure in mmHg.
RefTmpV = the characterization V(Tmp) voltage stored in EEPROM 450.
V(Tmp) = the measured temperature voltage in the agent optical bench.

It is to be noted that the calculations are made for both inspired and end-tidal nitrous oxide.

Having made the above calculations, the corrected absorption vector is determined by the following expression:

$$A'_j = A_j - ((P_{N20})(N_j)) \quad (6)$$

where, $A_j$ = uncorrected absorption vector for filter 1, 2, or 3.
$P_{N20}$ = the partial pressure of nitrous oxide in the agent gas pathway.
$N_j$ = the nitrous oxide correction coefficients stored in EEPROM 450.
j = the filter index variable: 1, 2, or 3.

Once the corrected absorption vectors have been calculated, the agent gas concentration may be calculated according to the expression:

$$P_g = \Sigma_l \Sigma_j (C_{glj}) (A'_j)^l \quad (7)$$

where, $P_g$ = the partial pressure of the agent gas enflurane, isoflurane, or halothane in mmHg.
l = the order for 1 to 3 of the equations.
j = the filter index variable: 1, 2, or 3.
$C_{glj}$ = the characterization coefficients stored in EEPROM 450.
g = gas type index: enflurane, isoflurane, or halothane.

After the partial pressures as can be seen, the double sum notation of equation (7) represents a matrix. The corrected absorption vector $A'_j$ is a variable which is second order when L=2 and third order when L=3 of the agent gases are calculated, they must be corrected for the effect of temperature on the pressure of the gas according to the following expression:

$$P_g' = P_g \frac{(V(Tmp))}{(RefTmpV)} \quad (8)$$

where, $P_g$ = the uncorrected partial pressure of the agent gas enflurane, isoflurane, or halothane.

V(Tmp) = the measured temperature voltage of the agent optical bench.

RefTmpV = the characterization V(Tmp) voltage stored in EEPROM 450.

g = gas type index: enflurane, isoflurane, or halothane.

Now that the partial pressures for the agent gases have been corrected for temperature, the concentrations are calculated by the following expression:

$$\% \; Conc_g = 100 \frac{(P_g')}{(P_{CELL})} \quad (9)$$

where,

% $Conc_g$ = the concentration for the agent gases enflurane, isoflurane, and halothane.

$P_g'$ = the partial pressure for halothane, enflurane, and isoflurane corrected for temperature.

$P_{CELL}$ = the pressure in mmHg in the agent gas pathway.

g = gas type index: enflurane, isoflurane, or halothane.

Once the calculations are made by microprocessor 806, they are transmitted to a connected apparatus for display of the concentration of the agent gases.

The terms and expressions which are employed here are terms of description and not limitation. There is no intention in the use of such terms and expressions to exclude the equivalents of the features shown and described, or portions thereof, it being recognized that various modifications are possible within the scope of the invention.

We claim:

1. An agent gas analyzer for simultaneously determining concentrations of N gases in a respiratory gas stream, where N>1, said agent gas analyzer comprising:

an optical bench including
at least one light source mounted to irradiate a portion of said respiratory gas stream with radiation,
means for separating said radiation into N different bands of wavelengths of said radiation, and
means for detecting the amount of radiation received, after passing through said portion of said respiratory gas stream, in each of said N different bands of wavelengths of said radiation;
means, coupled to said optical bench, for generating N electrical absorption signals representative of said amount of received radiation in said N bands; and
means, coupled to said means for generating, for computing simultaneously the concentrations of each of said N gases in the respiratory gas stream using matrix equations with a dimension of the matrix equal to N, and including said N electrical absorption signals as variables which are at least second order variables in said matrix equations.

2. The apparatus as recited in claim 1, wherein said at least second order variables include third order variables.

3. The apparatus of claim 1 further comprising:

a memory storing coefficients for said matrix equation, said coefficients varying according to the values of said electrical absorption signals; and
means for applying said electrical absorption signals to said memory to select a set of coefficients for use in said matrix equation.

4. The apparatus of claim 1 wherein said means for separating includes:

N filters having N discrete passbands of radiation wavelengths for selectively filtering radiation produced by said light source.

5. The apparatus of claim 1 wherein said means for computing determines said amount of radiation absorbed during periods when a rate of change of a reference gas in said respiratory gas stream is within a predetermined range and interpolates a value from values for absorption in one of said bands from previous and subsequent periods based on a time-weighted average when the amount of radiation absorbed in said one band is not detected in one of said periods.

6. The apparatus of claim 1 further comprising:

means for detecting the absorption of radiation in a reference band corresponding to absorption by a reference gas indicative of inspired and expired events in a breath cycle of said respiratory gas stream;
wherein said means for computing determines the occurrence of an inspired or expired event from the amount of radiation detected in said reference band and computes and displays said concentrations for a period of time corresponding to one of said inspired and expired events.

7. The apparatus of claim 6 wherein said reference gas is carbon dioxide.

8. The apparatus of claim 6 wherein said means for computing determines a sample period within one of said inspired and expired periods wherein the rate of change of absorption by said reference gas is within a predetermined range and computes the concentrations of each of said N gases from said amount of radiation detected during said sample period of time.

9. The apparatus of claim 6 wherein said means for determining the occurrence of an inspired or expired event includes means for determining whether the absorption in said reference band for said inspired and expired events crossed inspired and expired threshold levels, respectively.

10. The apparatus of claim 9 wherein said inspired and expired threshold levels are continually adjusted based upon both previous inspired and expired events.

11. An agent gas analyzer for determining concentrations of N agent gases in a respiratory gas stream, said agent gas analyzer comprising:

an optical bench including
at least one light source mounted to irradiate a portion of said respiratory gas stream with radiation,
means for separating said radiation into a reference band, corresponding to absorption by a reference gas indicative of inspired and expired events in a breath cycle of said respiratory gas stream, and N different agent bands of wavelengths of said radiation, and
means for detecting the absorption of radiation from radiation received, after passing through said portion of said respiratory gas stream, in said reference band; means, coupled to said optical bench, for determining the occurrence of an inspired or expired event from the amount of received radiation detected in said reference band;

means for detecting the amount of radiation absorbed by said respiratory gas stream in said N different agent bands; and means for computing and displaying said concentrations from said amounts of radiation in said agent bands absorbed for a period of time corresponding to one of said inspired and expired events wherein the rate of change of absorption by said reference gas is within a predetermined range.

12. An agent gas analyzer for determining concentrations of N gases in a respiratory gas stream, said agent gas analyzer comprising:

an optical bench including at least one light source mounted to irradiate a portion of said respiratory gas stream with radiation, means for separating said radiation into N different bands of wavelengths of said radiation, and means for detecting the absorption of radiation from radiation received, after passing through said portion of said respiratory gas stream, in as many of said N bands of wavelengths of said radiation as is possible during each of a plurality of measurement periods;

means, coupled to said optical bench, for interpolating a value from values for absorption in one of said bands from previous and subsequent periods to determine the absorption in said one band when absorption is not detected in one of said measurement periods and computing the concentrations of each of said N gases using detected and interpolated absorptions with multiple simultaneous equations.

13. The apparatus of claim 12 wherein said measurement period is one of an inspired and expired event in a breath cycle.

14. The apparatus of claim 12 wherein said multiple simultaneous equations are matrix equations with said absorptions being variables which are at least second order variables.

15. An agent gas analyzer for determining concentrations of N gases in a respiratory gas stream, where N>1, said agent gas analyzer comprising:

an optical bench including at least one light source mounted to irradiate a portion of said respiratory gas stream with radiation, means for separating said radiation into N different bands of wavelengths of said radiation, and means for detecting the absorption of said radiation from radiation received, after passing through said portion of said respiratory gas stream, in said N bands of wavelengths of said radiation;

means, coupled to said optical bench, for comparing a detected absorption in one of said N bands to criteria for one of an inspired and an expired event of a breath cycle;

means for determining whether said absorption for said one band is within said event; and means for computing the concentrations of each of said N gases during said event using detected absorptions with multiple simultaneous equations.

16. The apparatus of claim 15 wherein said means for detecting includes means for moving a filter for one of said N bands through said respiratory gas stream, such that said moving is synchronized with said event.

17. The apparatus of claim 15 wherein said criteria include determining whether the absorption levels for a reference gas cross threshold levels for inspired and expired events of a breath cycle.

18. The apparatus of claim 15 wherein said criteria include a predetermined range for a rate of change of said one band.

19. The apparatus of claim 18 wherein said one band corresponds to a reference gas.

20. The apparatus of claim 18 wherein said one band corresponds to an agent gas.

21. The apparatus of claim 18 wherein said multiple simultaneous equations are matrix equations with said absorptions being variables which are at least second order variables.

* * * * *